(12) United States Patent
Penichet et al.

(10) Patent No.: US 8,617,557 B2
(45) Date of Patent: Dec. 31, 2013

(54) ANTIBODY FUSION WITH IL-12 PROTEINS WITH DISRUPTED HEPARIN-BINDING ACTIVITY

(75) Inventors: Manuel L. Penichet, Los Angeles, CA (US); Rosendo Luria-Perez, Culver City, CA (US); Gustavo Helguera, Buenos Aires, AR (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/581,369

(22) PCT Filed: Mar. 11, 2011

(86) PCT No.: PCT/US2011/028099
§ 371 (c)(1),
(2), (4) Date: Aug. 27, 2012

(87) PCT Pub. No.: WO2011/112935
PCT Pub. Date: Sep. 15, 2011

(65) Prior Publication Data
US 2012/0321589 A1    Dec. 20, 2012

Related U.S. Application Data

(60) Provisional application No. 61/313,149, filed on Mar. 12, 2010.

(51) Int. Cl.
*A61K 39/00* (2006.01)
*C07K 16/46* (2006.01)

(52) U.S. Cl.
USPC ................................... 424/178.1; 530/391.7

(58) Field of Classification Search
None
See application file for complete search history.

(56) References Cited

U.S. PATENT DOCUMENTS

| 5,314,995 A | 5/1994 | Fell |
| 6,979,726 B1 | 12/2005 | von Hoegen |
| 7,736,652 B2 | 6/2010 | Penichet |
| 2003/0171551 A1 | 9/2003 | Rosenblatt |
| 2003/0187225 A1 | 10/2003 | Penichet |

FOREIGN PATENT DOCUMENTS

| WO | 9730089 A1 | 8/1997 |
| WO | 2008134879 A1 | 11/2008 |

OTHER PUBLICATIONS

International Search Report received in PCT/US2011/028099, mailed Dec. 7, 2011.
Ortiz-Sanchez, E. et al. (2008) "Antibody-cytokine Fusion Proteins: Applications in Cancer Therapy" Expert Opinion on Biological Therapy, 8(5):609-632. Abstract provided.
Helguera, G. et al. (2006) "Cytokines Fused to Antibodies and Their Combinations as Therapeutic Agents Against Different Peritoneal HER2/neu Expressing Tumors" Mol Cancer Ther. 5(4):1029-40.
Chang, C. et al. (2009) "Advances and Challenges in Developing Cytokine Fusion Proteins as Improved Therpeutics" Expert Opinion on Drug Discovery, 4(2):181-194. Abstract provided.
Najjam, S. et al. (1998) "Further Characterization of the Binding of Human Recombinant Interleukin 2 to Heparin and Identification of Putative Binding Sites" Glycobiology 8(5):509-516.
Hasan et al. (1999) "IL-12 Is a Heparin-Binding Cytokine" J of Immunol 162:1064-1070.
International Preliminary Report on Patentability and Written Opinion received in PCT/US2011/028099, issued Sep. 18, 2012.

Primary Examiner — Elly-Gerald Stoica
(74) Attorney, Agent, or Firm — Suznnah K. Sundby, Esq.; Smith, Gambrell & Russell, LLP

(57) ABSTRACT

Disclosed herein are polypeptides which comprise all or part of an antibody linked to all or part of a cytokine. The cytokine sequences of the polypeptides have a modified heparin binding region which disrupts, inhibits, or reduces the ability of the cytokine to bind a heparin compound as compared to a corresponding cytokine having an unmodified heparin binding region. Also disclosed are methods of treating cancer, inducing cell proliferation, and reducing the non-specific binding and/or non-specific localization of the polypeptides.

17 Claims, 16 Drawing Sheets

```
IL-12 wild type    RIQRKKEKMK
IL-12 R254A        ---A------
IL-12 K255A        ----A-----
IL-12 K256A        -----A----
IL-12 K258A        -------A--
IL-12 K260A        ---------A
```

Figure 1

```
NP_002178       H. sapiens      SEQ ID NO.:2    1   IWELKKDVYVVELDWYPDAP    20
XP_527101       P. troglodytes  SEQ ID NO.:3    1   IWELKKDVYVVELDWYPDAP    20
NP_001003292    C. lupus        SEQ ID NO.:4    1   IWELEKDVYVVELDWHPDAP    20
NP_776781       B. taurus       SEQ ID NO.:5    1   MWELEKNVYVVELDWYPDAP    20
NP_032378       M. musculus     SEQ ID NO.:6    1   MWELEKDVYVVEVDWTPDAP    20
NP_072133       R. norvegicus   SEQ ID NO.:7    1   MWELEKDVYVVEVDWRPDAP    20

NP_002178        21   GEMVVLTCDTPEED-GITWTLDQSSEVLGSGKTLTIQVKEFGDAGQYTC-   68
XP_527101        21   GEMVVLTCDTPEED-GITWTSDQSSEVLGSGKTLTIQVKEFGDAGQYTC-   68
NP_001003292     21   GEMVVLTCHTPEED-DITWTSAQSSEVLGSGKTLTIQVKEFGDAGQYTC-   68
NP_776781        21   GETVVLTCDTPEED-GITWTSDQSSEVLGSGKTLTIQVKEFGDAGQYTC-   68
NP_032378        21   GETVNLTCDTPEED-DITWTSDQRHGVIGSGKTLTITVKEFLDAGQYTC-   68
NP_072133        21   GETVTLTCDSPEED-DITWTSDQRRGVIGSGKTLTITVREFLDAGQYTC-   68

NP_002178        69   -HKGGEVLSHSLLLLHKKE-DGIWSTDILKDQKEPKNKTFLRCEAKNYSG   116
XP_527101        69   -HKGGEVLSHSLLLLHKKE-DGIWSTDILKDQKEPKTKTFLRCEAKNYSG   116
NP_001003292     69   -HKGGKVLSRSLLLIHKKE-DGIWSTDILKEQKESKNKIFLKCEAKNYSG   116
NP_776781        69   -HKGGEALSRSLLLLHKKE-DGIWSTDILKDQKEPKAKSFLKCEAKDYSG   116
NP_032378        69   -HKGGETLSHSHLLLHKKE-NGIWSTEILKNF---KNKTFLKCEAPNYSG   113
NP_072133        69   -HRGGETLSHSHLLLHKKE-NGIWSTEILKNF---KNKTFLKCEAPNYSG   113

NP_002178       117   RFTCWWLTTIST-DLTFSVKSSRGSSDPQGVTCGAATLSAERVRGDNKEY   165
XP_527101       117   RFTCWWLTTIST-DLTFSVKSSRGSSDPQGVTCGAATLSAERVRGDNKEY   165
NP_001003292    117   RFTCWWLTAIST-DLKFSVKSSRGFSDPQGVTCGAVTLSAERVRVDNRDY   165
NP_776781       117   HFTCWWLTAIST-DLKFSVKSSRGSSDPRGVTCGAALLSAEKVSLEHREY   165
NP_032378       114   RFTCSWLVQRNM-DLKFNIKSSSSSPDSRAVTCGMASLSAEKVTLDQRDY   162
NP_072133       114   RFTCSWLVHRNT-DLKFNIKSSSSSPESRAVTCGRASLSAEKVTLNQRDY   162

NP_002178       166   -EYSVECQEDSACPAAEESLPIEVMVDAVHKLKYENYTSSFFIRDIIKPD   214
XP_527101       166   -EYSVECQEDSACPAAEESLPIEVMVDAVHKLKYENYTSSFFIRDIIKPD   214
NP_001003292    166   KKYTVECQEGSACPSAEESLPIEVVVDAIHKLKYENYTSSFFIRDIIKPD   215
NP_776781       166   NKYTVECQEGSACPAAEESLLIEVVVEAVHKLKYENYTSSFFIRDIIKPD   215
NP_032378       163   EKYSVSCQEDVTCPTAEETLPIELALEARQQNKYENYSTSFFIRDIIKPD   212
NP_072133       163   EKYSVACQEDVTCPTAEETLPIELVVEAQQQNKYENYSTSFFIRDIIKPD   212

NP_002178       215   PPKNLQLKPLKNSRQVEVSWEYPDTWSTPHSYFSLTFCVQVQGKSKREKK   264
XP_527101       215   PPKNLQLKPLKNSRQVEVSWEYPDTWSTPHSYFSLTFCVQVQGKSKREKK   264
NP_001003292    216   PPTNLQLKPLKNSRHVEVSWEYPDTWSTPHSYFSLTFCVQAQGKNNREKK   265
NP_776781       216   PPKNLQLRPLKNSRQVEVSWEYPDTWSTPHSYFSLTFCVQVQGKNKREKK   265
NP_032378       213   PPKNLQMKPLKNS-QVEVSWEYPDSWSTPHSYFSLKFFVRIQRKKEKMKE   261
NP_072133       213   PPKNLQVKPLKNS-QVEVSWEYPDSWSTPHSYFSLKFFVRIQRKKEKTKE   261

NP_002178       265   --------DRVFTDKTSATVICRKNA---SISVRAQDRYYSSSWSEWASV   303
XP_527101       265   --------DRVFTDKTSATVICRKNA---SISVRAQDRYYSSSWSEWASV   303
NP_001003292    266   --------DRLCVDKTSAKVVCHKDA---KIRVQARDRYYSSSWSDWASV   304
NP_776781       266   ---------LFMDQTSAKVTCHKDA---NVRVQARDRYYSSFWSEWASV   302
NP_032378       262   TEEGCNQKGAFLVEKTSTEVQC-KGG---NVCVQAQDRYYNSSCSKWACV   307
NP_072133       262   TEEECNQKGAFLVEKTSAEVQC-KGA---NICVQAQDRYYNSSCSKWTCV   307

NP_002178       304   PCS-------------   306
XP_527101       304   PCS-------------   306
NP_001003292    305   SCS-------------   307
NP_776781       303   SCS-------------   305
NP_032378       308   PCRVRS----------   313
NP_072133       308   PCRGRS----------   313
```

Figure 2

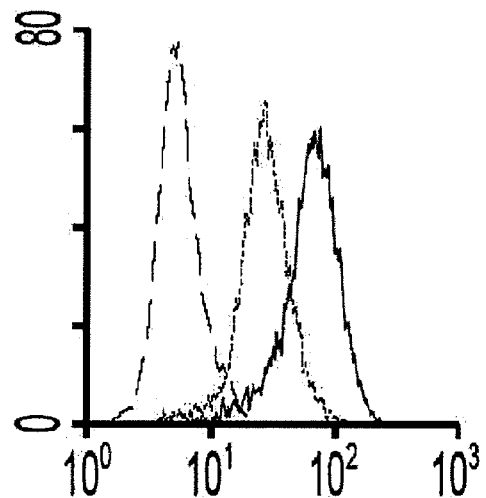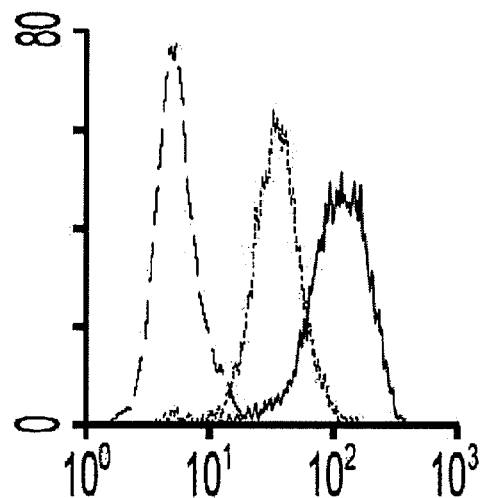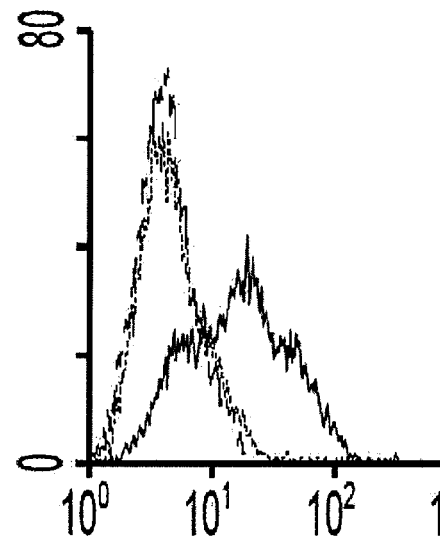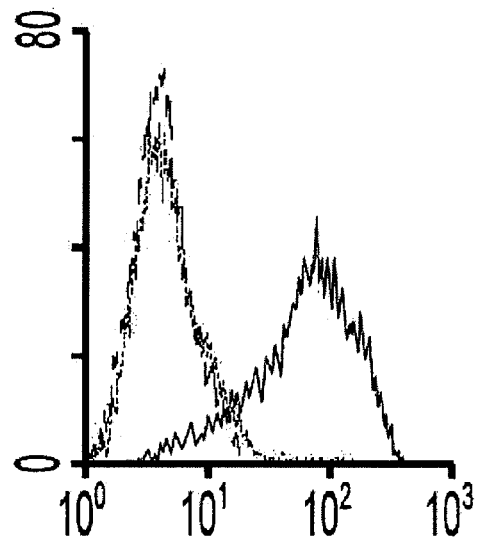
Figure 3C cont.

SEQUENCE LISTING

```
<160> NUMBER OF SEQ ID NOS: 14

<210> SEQ ID NO 1
<211> LENGTH: 10
<212> TYPE: PRT
<213> ORGANISM: Mus musculus

<400> SEQUENCE: 1

Arg Ile Gln Arg Lys Lys Glu Lys Met Lys
1               5                   10

<210> SEQ ID NO 2
<211> LENGTH: 306
<212> TYPE: PRT
<213> ORGANISM: Homo sapiens

<400> SEQUENCE: 2

Ile Trp Glu Leu Lys Lys Asp Val Tyr Val Val Glu Leu Asp Trp Tyr
1               5                   10                  15
```

```
Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
 50                      55                  60

Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                 85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
                180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
            275                 280                 285

Gln Asp Arg Tyr Tyr Ser Ser Ser Trp Ser Glu Trp Ala Ser Val Pro
    290                 295                 300

Cys Ser
305

<210> SEQ ID NO 3
<211> LENGTH: 306
<212> TYPE: PRT
<213> ORGANISM: Pan troglodytes

<400> SEQUENCE: 3

Ile Trp Glu Leu Lys Lys Asp Val Tyr Val Val Glu Leu Asp Trp Tyr
 1               5                  10                  15

Pro Asp Ala Pro Gly Glu Met Val Val Leu Thr Cys Asp Thr Pro Glu
            20                  25                  30

Glu Asp Gly Ile Thr Trp Thr Ser Asp Gln Ser Ser Glu Val Leu Gly
            35                  40                  45

Ser Gly Lys Thr Leu Thr Ile Gln Val Lys Glu Phe Gly Asp Ala Gly
 50                      55                  60

Gln Tyr Thr Cys His Lys Gly Gly Glu Val Leu Ser His Ser Leu Leu
 65                  70                  75                  80
```

-continued

```
Leu Leu His Lys Lys Glu Asp Gly Ile Trp Ser Thr Asp Ile Leu Lys
                 85                  90                  95

Asp Gln Lys Glu Pro Lys Thr Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305

<210> SEQ ID NO 4
<211> LENGTH: 307
<212> TYPE: PRT
<213> ORGANISM: Canis lupus familiaris

<400> SEQUENCE: 4

Ile Trp Glu Leu Glu Lys Asp Val Tyr Val Val Glu Leu Asp Trp His
1               5                   10                  15

Pro Asp Ala Pro Gly Glu Met Val Val Leu Thr Cys Asp Thr Pro Glu
            20                  25                  30

Glu Asp Asp Ile Thr Trp Thr Ser Ala Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Lys Val Leu Ser Arg Ser Leu Leu
65                  70                  75                  80

Leu Ile His Lys Lys Glu Asp Gly Ile Trp Ser Thr Asp Ile Leu Lys
                85                  90                  95

Glu Gln Lys Glu Ser Lys Asn Lys Ile Phe Leu Lys Cys Glu Ala Lys
            100                 105                 110

Asn Tyr Ser Gly Arg Phe Thr Cys Trp Trp Leu Thr Ala Ile Ser Thr
        115                 120                 125

Asp Leu Lys Phe Ser Val Lys Ser Ser Arg Gly Phe Ser Asp Pro Gln
    130                 135                 140
```

-continued

Gly Val Thr Cys Gly Ala Val Thr Leu Ser Ala Glu Arg Val Arg Val
145                 150                 155                 160

Asp Asn Arg Asp Tyr Lys Lys Tyr Thr Val Glu Cys Gln Glu Gly Ser
            165                 170                 175

Ala Cys Pro Ser Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
            195                 200                 205

Arg Asp Ile Ile Lys Pro Asp Pro Thr Asn Leu Gln Leu Lys Pro
210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Cys Val Gln Ala
            245                 250                 255

Gln Gly Lys Asn Asn Arg Glu Lys Lys Asp Arg Leu Cys Val Asp Lys
            260                 265                 270

Thr Ser Ala Lys Val Val Cys His Lys Asp Ala Lys Ile Arg Val Gln
            275                 280                 285

Ala Arg Asp Arg Tyr Tyr Ser Ser Ser Trp Ser Asp Trp Ala Ser Val
290                 295                 300

Ser Cys Ser
305

<210> SEQ ID NO 5
<211> LENGTH: 305
<212> TYPE: PRT
<213> ORGANISM: Bos taurus

<400> SEQUENCE: 5

Met Trp Glu Leu Glu Lys Asn Val Tyr Val Val Glu Leu Asp Trp Tyr
1               5                   10                  15

Pro Asp Ala Pro Gly Glu Thr Val Val Leu Thr Cys Asp Thr Pro Glu
            20                  25                  30

Glu Asp Gly Ile Thr Trp Thr Ser Asp Gln Ser Ser Glu Val Leu Gly
        35                  40                  45

Ser Gly Lys Thr Leu Thr Ile Gln Val Lys Glu Phe Gly Asp Ala Gly
50                  55                  60

Gln Tyr Thr Cys His Lys Gly Gly Glu Ala Leu Ser Arg Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Ala Lys Ser Phe Leu Lys Cys Glu Ala Lys
            100                 105                 110

Asp Tyr Ser Gly His Phe Thr Cys Trp Trp Leu Thr Ala Ile Ser Thr
            115                 120                 125

Asp Leu Lys Phe Ser Val Lys Ser Ser Arg Gly Ser Ser Asp Pro Arg
130                 135                 140

Gly Val Thr Cys Gly Ala Ala Leu Leu Ser Ala Glu Lys Val Ser Leu
145                 150                 155                 160

Glu His Arg Glu Tyr Asn Lys Tyr Thr Val Glu Cys Gln Glu Gly Ser
            165                 170                 175

Ala Cys Pro Ala Ala Glu Glu Ser Leu Leu Ile Glu Val Val Val Glu
            180                 185                 190

Ala Val His Lys Leu Lys Tyr Glu Asn Tyr Thr Ser Ser Phe Phe Ile
            195                 200                 205

```
Arg Asp Ile Ile Lys Pro Asp Pro Lys Asn Leu Gln Leu Arg Pro
    210                 215                 220

Leu Lys Asn Ser Arg Gln Val Glu Val Ser Trp Glu Tyr Pro Asp Thr
225                 230                 235                 240

Trp Ser Thr Pro His Ser Tyr Phe Ser Leu Thr Phe Cys Val Gln Val
                245                 250                 255

Gln Gly Lys Asn Lys Arg Glu Lys Lys Leu Phe Met Asp Gln Thr Ser
                260                 265                 270

Ala Lys Val Thr Cys His Lys Asp Ala Asn Val Arg Val Gln Ala Arg
                275                 280                 285

Asp Arg Tyr Tyr Ser Ser Phe Trp Ser Glu Trp Ala Ser Val Ser Cys
    290                 295                 300

Ser
305

<210> SEQ ID NO 6
<211> LENGTH: 313
<212> TYPE: PRT
<213> ORGANISM: Mus musculus

<400> SEQUENCE: 6

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
                20                  25                  30

Glu Asp Asp Ile Thr Trp Thr Ser Asp Gln Arg His Gly Val Ile Gly
            35                  40                  45

Ser Gly Lys Thr Leu Thr Ile Thr Val Lys Glu Phe Leu Asp Ala Gly
50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
                100                 105                 110

Gly Arg Phe Thr Cys Ser Trp Leu Val Gln Arg Asn Met Asp Leu Lys
            115                 120                 125

Phe Asn Ile Lys Ser Ser Ser Ser Pro Asp Ser Arg Ala Val Thr
130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
                260                 265                 270
```

```
Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser
305                 310

<210> SEQ ID NO 7
<211> LENGTH: 313
<212> TYPE: PRT
<213> ORGANISM: Rattus norvegicus

<400> SEQUENCE: 7

Met Trp Glu Leu Glu Lys Asp Val Tyr Val Val Glu Val Asp Trp Arg
1               5                   10                  15

Pro Asp Ala Pro Gly Glu Thr Val Thr Leu Thr Cys Asp Ser Pro Glu
            20                  25                  30

Glu Asp Asp Ile Thr Trp Thr Ser Asp Gln Arg Arg Gly Val Ile Gly
        35                  40                  45

Ser Gly Lys Thr Leu Thr Ile Thr Val Arg Glu Phe Leu Asp Ala Gly
    50                  55                  60

Gln Tyr Thr Cys His Arg Gly Gly Glu Thr Leu Ser His Ser His Leu
65              70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val His Arg Asn Thr Asp Leu Lys
        115                 120                 125

Phe Asn Ile Lys Ser Ser Ser Ser Pro Glu Ser Arg Ala Val Thr
130                 135                 140

Cys Gly Arg Ala Ser Leu Ser Ala Glu Lys Val Thr Leu Asn Gln Arg
145                 150                 155                 160

Asp Tyr Glu Lys Tyr Ser Val Ala Cys Gln Glu Asp Val Thr Cys Pro
                165                 170                 175

Thr Ala Glu Glu Thr Leu Pro Ile Glu Leu Val Val Glu Ala Gln Gln
            180                 185                 190

Gln Asn Lys Tyr Glu Asn Tyr Ser Thr Ser Phe Phe Ile Arg Asp Ile
        195                 200                 205

Ile Lys Pro Asp Pro Lys Asn Leu Gln Val Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Thr Lys Glu Thr Glu Glu Cys Asn Gln Lys Gly Ala Phe
            260                 265                 270

Leu Val Glu Lys Thr Ser Ala Glu Val Gln Cys Lys Gly Ala Asn Ile
        275                 280                 285

Cys Val Gln Ala Gln Asp Arg Tyr Tyr Asn Ser Ser Cys Ser Lys Trp
    290                 295                 300

Thr Cys Val Pro Cys Arg Gly Arg Ser
305                 310

<210> SEQ ID NO 8
<211> LENGTH: 24
```

```
<212> TYPE: PRT
<213> ORGANISM: Homo sapiens

<400> SEQUENCE: 8

Lys Tyr Glu Asn Tyr Thr Ser Ser Phe Phe Ile Arg Asp Ile Ile Lys
1               5                   10                  15

Pro Asp Pro Pro Lys Asn Leu Gln
            20

<210> SEQ ID NO 9
<211> LENGTH: 20
<212> TYPE: PRT
<213> ORGANISM: Homo sapiens

<400> SEQUENCE: 9

Val Glu Val Ser Trp Glu Tyr Pro Asp Thr Trp Ser Thr Pro His Ser
1               5                   10                  15

Tyr Phe Ser Leu
            20

<210> SEQ ID NO 10
<211> LENGTH: 12
<212> TYPE: PRT
<213> ORGANISM: Homo sapiens

<400> SEQUENCE: 10

Val Gln Val Gln Gly Lys Ser Lys Arg Glu Lys Lys
1               5                   10

<210> SEQ ID NO 11
<211> LENGTH: 12
<212> TYPE: PRT
<213> ORGANISM: Canis lupus familiaris

<400> SEQUENCE: 11

Val Gln Ala Gln Gly Lys Asn Asn Arg Glu Lys Lys
1               5                   10

<210> SEQ ID NO 12
<211> LENGTH: 12
<212> TYPE: PRT
<213> ORGANISM: Bos taurus

<400> SEQUENCE: 12

Val Gln Val Gln Gly Lys Asn Lys Arg Glu Lys Lys
1               5                   10

<210> SEQ ID NO 13
<211> LENGTH: 12
<212> TYPE: PRT
<213> ORGANISM: Mus musculus

<400> SEQUENCE: 13

Val Arg Ile Gln Arg Lys Lys Glu Lys Met Lys Glu
1               5                   10

<210> SEQ ID NO 14
<211> LENGTH: 12
<212> TYPE: PRT
<213> ORGANISM: Rattus norvegicus

<400> SEQUENCE: 14

Val Arg Ile Gln Arg Lys Lys Glu Lys Thr Lys Glu
1               5                   10
```

ANTIBODY FUSION WITH IL-12 PROTEINS WITH DISRUPTED HEPARIN-BINDING ACTIVITY

CROSS-REFERENCE TO RELATED APPLICATIONS

This application claims the benefit of U.S. Patent Application Ser. No. 61/313,149, filed 12 Mar. 2010, which is herein incorporated by reference in its entirety.

ACKNOWLEDGEMENT OF GOVERNMENT SUPPORT

This invention was made with Government support under Grant Nos. CA057152 and TW000013, awarded by the National Institutes of Health. The Government has certain rights in this invention.

REFERENCE TO A SEQUENCE LISTING SUBMITTED VIA EFS-WEB

The content of the ASCII text file of the sequence listing named "20110311_034044_083WO1_ST25" which is 17.6 kb in size was created on 11 Mar. 2011 and electronically submitted via EFS-Web herewith the application is incorporated herein by reference in its entirety.

BACKGROUND OF THE INVENTION

1. Field of the Invention

The present invention generally relates to polypeptides comprising an antibody sequence linked to a cytokine sequence and methods of making and using thereof.

2. Description of the Related Art

Interleukin 12 (IL-12) is a heterodimeric cytokine composed of p35 and p40 subunits which are encoded by 2 separate genes, IL-12A and IL-12B, respectively. The natural activity of IL-12 is likely influenced by its heparin binding activity which retains IL-12 close to local tissue compartments to execute its paracrine effects. See e.g. Hasan et al. (1999) J. Immunol. 162:10064-1070.

Both IL-2 and IL-12 have been used for the immunotherapy of cancer. Antibody-(IL-2) fusion proteins have been used in successful anti-tumor experiments using animal models. See Penichet & Morrison (2001) J Immunol Met 248:91-101. Numerous studies have explored various combinations of antibodies and, e.g., IL-2, as direct targeting agents of tumor cells. For example, a tumor specific antibody-(IL-2) fusion protein was previously developed, and comprised a human IgG3 specific for the idiotype (Id) of the immunoglobulin expressed on the surface of the B cell lymphoma 38C13 with human IL-2 fused at the end of the $C_H3$ domain. See Penichet et al. (1998) J Interferon Cytokine Res 18:597-607. Other examples of antibody fusion molecules include a humanized anti-HER2/neu IgG3 fused to IL-12 and a recombinant IgG3-(IL-2) fusion protein. See Peng et al. (1999) J Immunol 163:250-8); and Penichet et al. (2001) Human Antibodies 10:43-49.

In all of the above work, it is important to note that the antibody-cytokine fusion proteins containing IL-2 and IL-12 have been used as direct anti-tumor agents which are expected to directly targeted tumors in animal models. The antibody fusion proteins bind to antigens on tumor surfaces, thus increasing the local concentration of the antibody-cytokine fusion protein in the tumor microenvironment.

Unfortunately, although anti-tumor responses were observed in some subjects, the systemic injection of free IL-2 or IL-12 often results in severe toxicity due to the high dose that is required to induce the anti-tumor immune response. Although fusing the cytokine to an antibody is expected to better target the cytokine into the tumor reducing its site effects (toxicity) we have also found that these antibody-cytokine fusion proteins also exhibit the heparin-binding activity of the fused cytokines (IL-2 or IL-12), which makes them bind non-specifically to a broad variety of cells throughout the body and the extracellular matrix (ECM) of normal tissues. This heparin-binding activity is expected to reduce the capacity of the antibody-cytokine fusion proteins to specifically target the tumors due to its retention outside the tumor microenvironment, which may also result in unfavorable side effects.

Therefore, a need still exists for effective therapeutics.

SUMMARY OF THE INVENTION

In some embodiments, the present invention provides Ab-modC proteins which comprise an antibody sequence, e.g. all or part of an antibody, linked to a cytokine sequence, e.g. all or part of a cytokine, which has a modified heparin binding region which disrupts, inhibits, or reduces the ability of the cytokine sequence to bind a heparin compound as compared to a corresponding cytokine having an unmodified heparin binding region. In some embodiments, the antibody sequence may be specific for a tumor associated antigen, such as epidermal growth factor receptor (EGFR), transferrin receptor (CD71), mucin 1 (MUC1), prostate-specific membrane antigen (PMSA), CD19, CD20, CD33, CD40, CD52, and the like. In some embodiments, the antibody sequence is a human antibody sequence or a human chimeric antibody sequence. In some embodiments, the cytokine is an immunostimulatory cytokine. In some embodiments, the cytokine is IL-2, IL-3, IL-4, IL-5, IL-6, IL-7, IL-8, IL-10 and IL-12, or granulocyte/macrophage colony-stimulating factor (GM-CSF). In some embodiments, the cytokine is a human cytokine. In some embodiments, the modified heparin binding region does not significantly or substantially reduce the immunostimulatory activity of the cytokine and/or the Ab-modC protein. In some embodiments, the modified heparin binding region of the Ab-modC protein comprises, consists essentially of, or consists of the following formula I:

V-X1-X2-Q-X3-K*-X4-X5-X6-X7-K*-X8 (I)

wherein X1 is R or Q,
X2 is V, A, or I,
X3 is G or R*,
X4 is S, N, or K*,
X5 is K*, N, or E,
X6 is R or K,
X7 is E, M, or T, and
X8 is K* or E, and wherein one or more amino acid residues designated with an "*" are substituted with a non-polar amino acid residue selected from the group consisting of A, G, I, L, M, F, P, and V and other amino acid residues which result in a decrease in heparin binding as compared to the corresponding wild type IL-12. In some embodiments, the cytokine sequence exhibits immunostimulatory activity which is consistent with the corresponding wild type cytokine which does not have a modified heparin binding region. In some embodiments, the cytokine sequence further comprises a first amino acid sequence having at least 90%, 91%, 92%, 93%, 94%, 95%, 96%, 97%, 98%, 99%, or 100% identity to KYENYTSSFFIRDIIKPDP- PKNLQ (SEQ ID NO:8), and/or a second amino acid sequence having at least 90%, 91%, 92%, 93%, 94%, 95%, 96%, 97%, 98%, 99%, or 100% identity to VEVSWEYP-DTWSTPHSYFSL (SEQ ID NO:9). In some embodiments, the antibody sequence is specific for HER2/neu.

In some embodiments, the present invention provides compositions and kits comprising one or more of the Ab-modC proteins as disclosed herein.

In some embodiments, the present invention provides nucleic acid molecules (and their complements) which encode the Ab-modC proteins as disclosed herein. In some embodiments, the present invention provides compositions comprising one or more of the nucleic acid molecules as disclosed herein. In some embodiments, the present invention provides vectors, host cells and kits which contain the nucleic acid molecules as disclosed herein.

In some embodiments, the present invention provides methods of treating a subject having cancer which comprises administering to the subject one or more of the Ab-modC proteins as disclosed herein.

In some embodiments, the present invention provides methods of inducing cell proliferation in a cell which comprises contacting the cell one or more of the Ab-modC proteins as disclosed herein.

In some embodiments, the present invention provides methods of reducing the non-specific binding and/or the non-specific localization of an antibody sequence fused to a cytokine sequence having a heparin binding region which comprises substituting one or more of the amino acid residues in the heparin binding region which results in a reduction in the ability of the cytokine sequence to bind a heparin compound.

In some embodiments, the present invention provides use of one or more Ab-modC proteins as disclosed herein to treat a subject in need thereof. In some embodiments, the present invention provides use of one or more Ab-modC proteins as disclosed herein for the manufacture of a medicament for treating a subject in need thereof. In some embodiments, the present invention provides use of one or more Ab-modC proteins as disclosed herein for the manufacture of a medicament for treating a subject in need thereof, wherein the medicament is prepared to be administered in a dosage regime, e.g. amount, suitable for treating the subject.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1 shows the proposed heparin binding region of wild type IL-12 (SEQ ID NO:1) and the amino acid substitutions for the modified IL-12 sequences exemplified herein.

FIG. 2 shows the aligned sequences of Accession Numbers P_002178 (SEQ ID NO:2), XP_527101 (SEQ ID NO:3), NP_001003292 (SEQ ID NO:4), NP_776781 (SEQ ID NO:5), NP_032378 (SEQ ID NO:6), and NP_072133 (SEQ ID NO:7).

FIG. 3A are graphs showing anti-HER2/neu IgG3-(modIL-12) binding to heparin. D2F2 murine mammary cancer cells ($2.5\times10^5$) were co-incubated during 4 hrs at 4° C. in the presence (dotted line) or absence (black line) of 1 USP/ml of heparin with 4 μg/ml of anti-DNS IgG3 (isotype control), anti-HER2/neu IgG3, anti-HER2/neu IgG3-(IL-12) or each one of the anti-HER2/neu IgG3-(modIL-12) followed by rabbit anti-human kappa conjugated to FITC and the samples analyzed by flow cytometry. Only mutants R254A and K258A are shown. This study was conducted using purified proteins. Results are representative of three independent experiments.

FIG. 3B are graphs showing anti-HER2/neu IgG3-(modIL-12) binding to heparin. D2F2 murine mammary cancer cells ($2.5\times10^5$) were co-incubated during 3 hrs at 4° C. in the presence (dotted line) or absence (black line) of 1 USP/ml of heparin with supernatant containing 1 μg of anti-DNS IgG3 (IgG3 isotype control), anti-HER2/neu IgG3 (IgG3), anti-HER2/neu IgG3-(IL-12), or each one of the anti-HER2/neu IgG3-(modIL-12) (only mutants R254A and K258A are shown) followed by rabbit anti-human kappa conjugated to FITC and the samples analyzed by flow cytometry. This study was conducted using proteins in tissue culture supernatant (before purification). Results are representative of three independent experiments.

FIG. 3C are graphs showing anti-HER2/neu IgG3-(modIL-12) binding to heparin using a flow cytometry assay. $2.5\times10^5$ D2F2-E2 murine mammary cancer cells expressing human HER2/neu (top) or the parental D2F2 not expressing the antigen (bottom) were co-incubated during 4 hrs at 4° C. in the presence (dotted line) or absence (black line) of 1 USP/ml of heparin with 4 μg of (IgG3 isotype control), anti-HER2/neu IgG3-(IL-12), or each one of the anti-HER2/neu IgG3-(modIL-12) followed by rabbit anti-human kappa conjugated to FITC and the samples analyzed by flow cytometry.

FIG. 4A is a graph showing the ELISA analysis of heparin binding activity of anti-HER2/neu IgG3-(modIL-12). Low molecular weight heparin was dissolved in PBS at 25 μg/ml and incubated on BD Heparin binding plates overnight at room temperature. The plates coated with heparin were washed with PBS and blocked with 3% BSA in PBS blocking solution for one hour at 37° C., followed by washing with PBS. Then, the anti-HER2/neu IgG3, anti-HER2/neu IgG3-(IL-12) or anti-HER2/neu IgG3-(modIL-12) were incubated in triplicates using 2-fold serial dilutions ranging from 5-0.04 μg/ml for 2 hours at 37° C. Only mutants R254A and K258A are shown. The binding was detected using a goat anti-human kappa conjugated to alkaline phosphatase. The absorbance was measured after 60 min incubation with substrate. Error bars are mean±SD of triplicate measurements. This study was conducted using purified proteins. Mutant R254A showed significantly lower values ($p<0.033$, Student's t-test) compared to anti-HER2/neu IgG3-(IL-12) as positive control. The graph is a representative result of two independent experiments.

FIG. 4B is a graph showing the ELISA analysis of heparin binding activity of anti-HER2/neu IgG3-(modIL-12). Heparin sodium salt (200 μg/ml was dissolved in PBS and incubated on BD Heparin binding plates overnight at room temperature. After blocking with 3% BSA in PBS, supernatant containing the anti-anti-HER2/neu IgG3 (IgG3), anti-HER2/neu IgG3-(IL-12), or each one of the anti-HER2/neu IgG3-(modIL-12) (only mutants R254A and K258A are shown) were incubated in triplicates using 2-fold serial dilutions ranging from 0.1-0.01 μg/ml for 2 hours at 37° C. The binding was detected using a goat anti-human kappa conjugated to alkaline phosphatase. Absorbances were measured after 120 minutes incubation with substrate. This study was conducted using proteins in tissue culture supernatant (before purification). The graph is a representative result of two independent experiments. Error bars are mean±SD of duplicate measurements.

DETAILED DESCRIPTION OF THE INVENTION

Figure 3A:
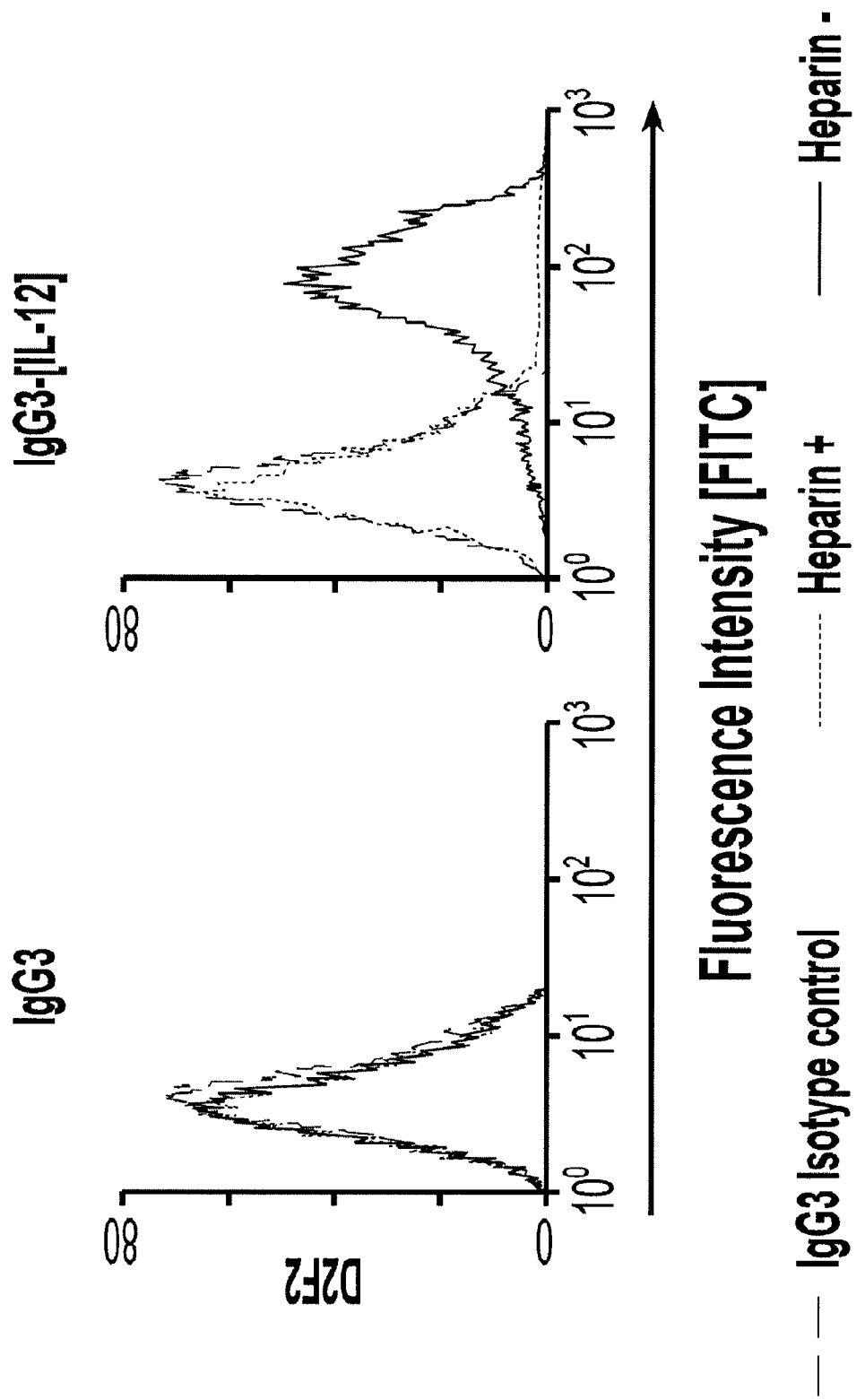
Figure 3A:
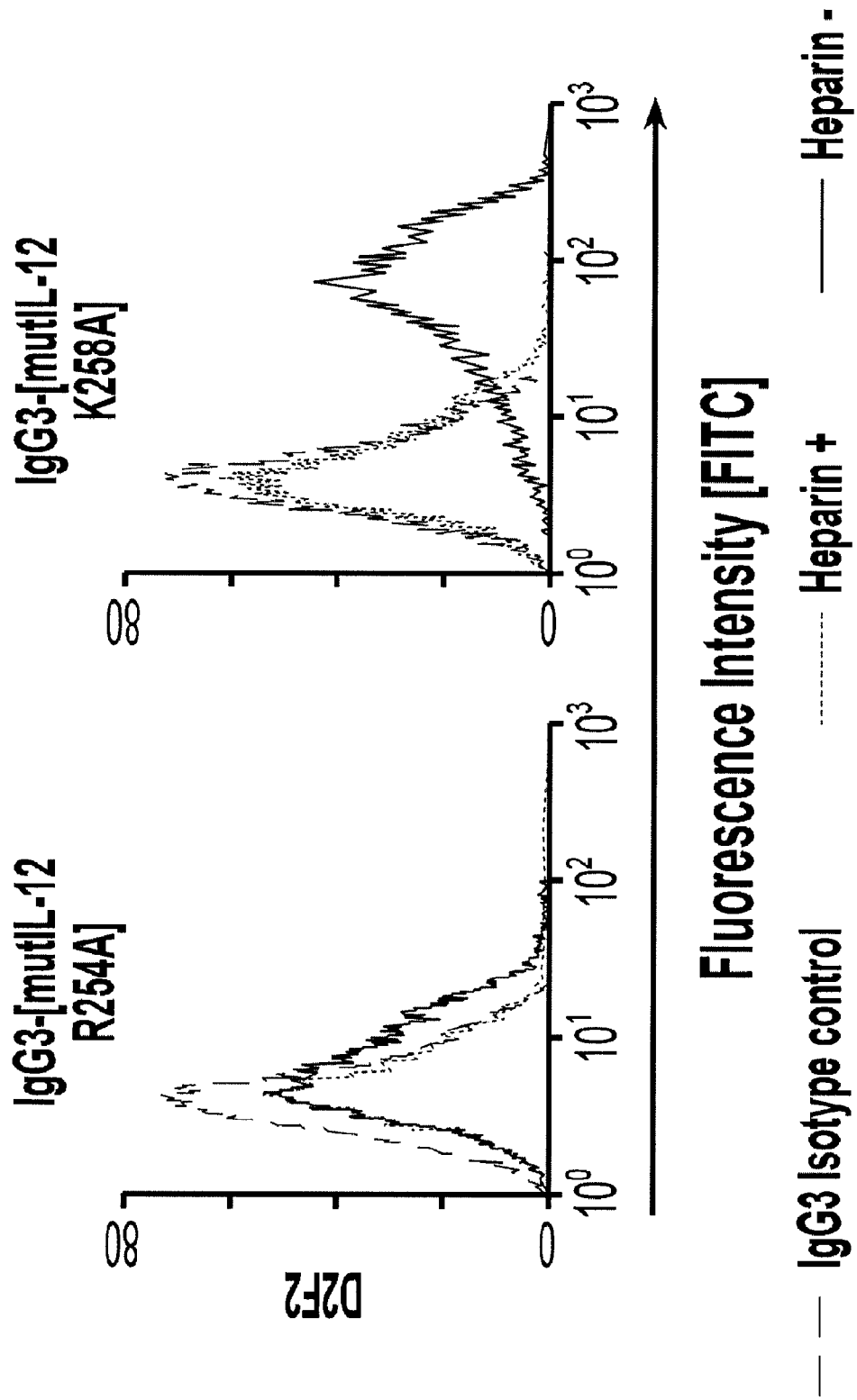

The present invention provides polypeptides comprising an antibody sequence linked to a cytokine sequence which exhibit a reduced ability to bind a heparin compound. In particular, the cytokine sequence is a modified, e.g. mutated, cytokine sequence which exhibits a reduced ability to bind a heparin compound as compared to the corresponding wild type cytokine which may or may not be similarly linked to an antibody sequence. The antibody sequence may be linked to the cytokine sequence by a covalent bond or a non-covalent bond. In some embodiments, the antibody sequence may be linked to the cytokine sequence with a linker known in the art. In some embodiments, the linker may be one or more amino acid residues. In some embodiments, the antibody sequence may be directly fused to the cytokine sequence using methods known in the art.

As used herein, a "heparin compound" includes glycosaminoglycans (GAG) such as heparin, heparan sulfate (HS), heparan sulfate proteoglycan (HSPG), perlecan, agrin, collagen XVIII, syndecan and glypican. It is noted, however, that heparin is used in the experiments herein as model of HS.

As used herein, a "cytokine" refer to an immunomodulating agent which includes interleukins, such as IL-2, IL-3, IL-4, IL-5, IL-6, IL-7, IL-8, IL-10 and IL-12, and granulocyte/macrophage colony-stimulating factor (GM-CSF). As provided herein, the cytokine sequences of the polypeptides of the present invention are modified, e.g. genetically modified, to have a reduced ability to bind a heparin compound as compared to its corresponding wild type form. Such modified cytokine sequences are generically designated as "modC", e.g. "Ab-modC proteins" refer to polypeptides having an antibody sequence linked to a modified cytokine sequence, and include interleukin mutants, such as the IL-12 mutants exemplified herein.

Although various IL-12 mutants are used herein to exemplify the cytokines of the Ab-modC proteins according to the present invention, any wild type cytokine sequence which exhibits an ability to bind a heparin compound may be modified, e.g. mutated, to exhibit a reduced ability to bind the heparin compound and then used as the modified cytokine sequence in an Ab-modC protein according to the present invention.

As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin, e.g. antibody, structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. As used herein, an "antibody" can be an intact immunoglobulin or a well characterized fragment thereof which may be produced by digestion with various peptidases or recombinant techniques known in the art. See Fundamental Immunology, W. E. Paul, ed., Raven Press, New York (1999). The term "antibody" also includes single chain antibodies, e.g. single chain Fv (sFv or scFv) antibodies in which a variable heavy and a variable light chain are joined together (directly or through a peptide linker) to form a continuous polypeptide.

Although an anti-HER2/neu antibody is used herein to exemplify the antibody sequence of the Ab-modC proteins according to the present invention, the sequence of any antibody or fragment thereof which is to be administered to a subject is contemplated herein. In some embodiments, the antibody sequence is specific for a tumor antigen. Examples of tumor antigens include epidermal growth factor receptor (EGFR), transferrin receptor (CD71), mucin 1 (MUC1), prostate-specific membrane antigen (PMSA), CD19, CD20, CD33, CD40, CD52, and the like.

The Ab-modC proteins of the present invention may be used in pharmaceutical compositions and therapeutic treatments to target a target antigen and elicit or enhance an immune response (humoral and/or cellular) within a subject against the target antigen and/or a target cell, i.e. a cell which expresses the target antigen. In other words, in some embodiments, the Ab-modC proteins act as adjuvants to elicit and/or enhance an immune response against a target antigen and/or a target cell. The Ab-modC protein according to the present invention may be bound or conjugated to another compound or composition such as a bead, an aggregate of antigens, liposomes, viral vectors, nanopolymers, nanoparticles, and the like.

As used herein, a "subject" refers to a mammal, preferably a human who may be a patient, e.g. under the care of a physician.

As used herein, an "antigen" refers to a molecule or composition which induces an immune response in a subject when administered thereto. A "target antigen" refers to an antigen which is a target of interest, i.e. an antigen which is specifically recognized by a given antibody. In some embodiments, the target antigen is a tumor antigen, e.g. HER2/neu, presented by or on a tumor cell or shed from a tumor cell or an antigen presented by or on an infectious organism such as a virus, a bacteria, e.g. a protein A antigen from *Staphylococcus aureus*, a fungus, a prion, a parasite, an autoimmune disorder, and the like. In some embodiments, the target antigen is a tumor associated antigen.

The term "pharmaceutical composition" refers to a composition suitable for pharmaceutical use in a subject. A pharmaceutical composition generally comprises an effective amount of an active agent, e.g. an Ab-modC protein according to the present invention, and a pharmaceutically acceptable carrier, e.g. a buffer, adjuvant, and the like.

The term "effective amount" refers to a dosage or amount sufficient to produce a desired result. The desired result may comprise an objective or subjective improvement in the recipient of the dosage or amount, e.g. long-term survival, decrease in number and/or size of tumors, effective prevention of a disease state, and the like.

The methods and compositions relating to HER2/neu and/or breast cancer are used to exemplify that Ab-modC proteins according to the present invention can lead to humoral and/or cellular immune responses in subjects and can therefore be used in therapeutic and/or prophylactic treatments. Nevertheless, other methods and compositions which relate to other antigens and diseases and/or infections are contemplated herein.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as an Ab-modC protein or composition thereof, which when administered to a subject who does not display signs or symptoms of a pathology, disease or disorder (or who displays only early signs or symptoms of a pathology, disease, or disorder) diminishes, prevents, or decreases the risk of the subject developing the pathology, disease, or disorder. A "prophylactically useful" agent or compound, e.g. an Ab-modC protein, refers to an agent or compound that is useful in diminishing, preventing, treating, or decreasing development of a pathology, disease or disorder.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as an Ab-modC protein or composition thereof, which eliminates or diminishes signs or symptoms of a pathology, disease or disorder, when administered to a subject suffering from such signs or symptoms. A "therapeutically useful" agent or compound, e.g. an Ab-modC protein, indicates that an agent or compound is useful in diminishing, treating, or eliminating such signs or symptoms of the pathology, disease or disorder.

An Ab-modC protein according to the present invention is capable of eliciting an immune response against a target antigen as well as other antigens which are closely related to the target antigen, e.g. structurally and/or conformationally similar to the target antigen. For example, since HER2/neu has high homology with other growth factor receptors, such as epidermal growth factor receptors 1, 3, and 4 (EGFR1, EGFR3, EGFR4), the elicited immune response is optionally directed against these other antigens.

In some embodiments, the Ab-modC proteins may be used in prophylactic treatments. For example, a subject at risk of developing a disease or being exposed to an infectious agent or organism may be administered an Ab-modC protein according to the present invention, wherein the antibody sequence is specific for a target antigen of the infectious agent or organism. For example, a subject having a medical history which suggests that the subject has a high probability of developing breast cancer may be administered an Ab-modC protein comprising an antibody sequence specific for HER2/neu fused to a modified cytokine sequence (anti-HER2/neu-modC), e.g. anti-HER2/neu IgG3-(modIL) or (modIL)-anti-HER2/neu IgG3, wherein "modIL" is a modified, e.g. mutant, interleukin which has a reduced ability to bind a heparin compound. In some embodiments, the cytokine sequence is fused to the carboxy terminus or amino terminus of the heavy chain. However, the cytokine sequence can also be linked to the carboxy terminus or amino terminus of the light chain or to other domains of the heavy or light chain. These and other structures known in the art, such as disclosed in Helguera et al. (2006) Mol Cancer Ther 5:1029-1040, which is herein incorporated by reference in its entirety, are contemplated herein. In some embodiments, the subject may be administered an amount of HER2/neu antigen, alone or in combination, with the anti-HER2/neu-modC.

In some embodiments, the Ab-modC proteins may be used in therapeutic treatments. For example, a subject who has been diagnosed as having a disease or being infected with an infectious agent or organism may be administered an Ab-modC protein according to the present invention, wherein the antibody sequence is specific for a target antigen of the infectious agent or organism. For example, a subject who has been diagnosed with having breast cancer may be administered an Ab-modC protein comprising an antibody sequence specific for HER2/neu fused to a modified cytokine sequence (anti-HER2/neu-modC), e.g. anti-HER2/neu IgG3-(modIL) or (modIL)-anti-HER2/neu IgG3, wherein "modIL" is a modified, e.g. mutant, interleukin which has a reduced ability to bind a heparin compound. In some embodiments, the subject may be administered an amount of HER2/neu antigen, alone or in combination, with the anti-HER2/neu-modC.

In some embodiments, an Ab-modC protein, e.g. anti-HER2/neu-modC, is administered in combination with one or more known therapeutic compounds and/or strategies, such as trastuzumab (HERCEPTIN, Genentech, San Francisco, Calif.). In some embodiments, an Ab-modC protein, e.g. anti-HER2/neu-modC, is administered in place of one or more known therapeutic compounds and/or strategies. In some embodiments, different Ab-modC proteins can be used in conjunction with each other. For example, in some treatment regimens different Ab-modC proteins can be administered to a subject in the same course of treatment.

In some embodiments, the Ab-modC proteins may be used for ex vivo generation of mature dendritic cells. For example, dendritic cells obtained from a subject are treated (in vitro) with one or more Ab-modC proteins and the target antigen. Then, the mature and programmed dendritic cells are re-implanted into the subject.

In some embodiments, the Ab-modC proteins deliver the target antigen to a dendritic cell (DC) or to another appropriate antigen presenting cell (APC) through the interaction of the Ab-modC protein with surface receptors on the DC or APC such as GM-CSF, IL-2, IL-12 receptors, and the like. Depending upon, e.g. the specific modified cytokine, the presentation of the antigen to the DC or APC may lead to a potent activation of one or both arms of the immune response, i.e. cellular ($T_H1$) and humoral ($T_H2$). Such activation may produce a significant immuno-protective response when a subject who was previously administered the Ab-modC protein is challenged with the same target antigen or a closely related antigen.

In some embodiments, the immunostimulatory activities of the Ab-modC proteins contribute to the enhancement of the immune response against the target antigen, e.g. IL-2-cell proliferative signal, GMCSF-APC activation and IL-12-deviation to $T_H1$, and the like. In some embodiments, the immunostimulatory activities of the modified cytokines of the Ab-modC proteins are consistent with, i.e. the same, substantially similar, or greater than, the immunostimulatory activities of their wild type counterparts. In other words, a modified cytokine has a reduced ability to bind heparin compounds, yet exhibits an immunostimulatory activity which is consistent with that of the wild type cytokine, i.e. the modified cytokine exhibits an immunostimulatory activity which is the same, substantially similar, more than or less than that of the wild type cytokine as determined using assays known in the art, which may be in vivo and/or in vitro. In some embodiments, the modified cytokine of an Ab-modC protein according to the present invention may exhibit a reduced cytokine activity in in vitro assays, but due to its reduced ability to bind heparin compounds (in vitro and/or in vivo), the Ab-modC protein may exhibit an immunostimulatory activity in vivo that is the same or better than that of the corresponding wild type cytokine (this may be due to the superior targeting and potentially less unfavorable side effects of the Ab-modC proteins of the present invention).

While anti-HER2/neu-modC proteins are exemplified herein, the present invention encompasses various Ab-modC proteins comprising other modified cytokines linked to other antibodies and methods thereof. In other words, depending upon the specific condition and/or disease being treated, various combinations of modified cytokines and antibodies, e.g. different antibody fragments, antibodies of different isotype, and different antibodies with specificity against different antigens, are contemplated herein.

For example, Ab-modC proteins specific for the extracellular domain of the human tumor associated antigen HER2/neu ($ECD^{HER2}$) were constructed and used in the Examples detailed below. These proteins were composed of human IgG3 containing the variable region of trastuzumab (HERCEPTIN, Genentech, San Francisco, Calif.) genetically fused to interleukin-12 (IL-12, wild type) and IL-12 mutants (modIL-12).

The antibody sequences utilized in the examples herein are not to be construed as limiting. For example, other antibodies and fragments thereof against other target antigens, e.g. bacterial antigens, viral antigens, tumor associated antigens, *mycoplasm* antigens, antigens of parasites, prions, autoimmune disorders, and the like, may be employed as the antibody sequence in the Ab-modC proteins of the present invention. In addition, the antibody sequence of the Ab-modC proteins herein need not be an entire (whole) antibody. Instead, the antibody sequences of the Ab-modC proteins can be Fab, Fab', $F(ab)_2$, $F(ab')_2$, Fv, scFv, an antibody fragment, or a combination thereof. The antibody sequences of the Ab-modC proteins may also be scaffold, aptamers, and ligands acting as carriers. In some embodiments, the antibody sequences of the Ab-modC proteins comprise all or part of an immunoglobin molecule and/or all or part of an immunoglobin variable region, i.e. the area of specificity for the target antigen. In some embodiments, the antibody sequences of the Ab-modC proteins optionally comprise one or more regions encoded by a V gene, a D gene and/or a J gene.

In some embodiments, the antibody sequences of the Ab-modC proteins are IgG molecules or fragments thereof. In some embodiments, the antibody sequences of the Ab-modC proteins are IgM, IgA, IgD, IgE molecules or fragments thereof. In addition, all possible isotypes of the various immunoglobins are contemplated herein. In addition to choice in selection of the type of immunoglobin and isotype, the hinge regions may be modified or selected using methods known in the art to provide flexibility between the different domains of the Ab-modC proteins. See, e.g., Penichet, et al. (2001) J Immunol Methods 248:91-101, which is herein incorporated by reference.

As used herein, a "cytokines" refer to immunomodulating agents which include interleukins, such as IL-2, IL-3, IL-4, IL-5, IL-6, IL-7, IL-8, IL-10 and IL-12, and granulocyte/macrophage colony-stimulating factor (GM-CSF). In some embodiments, the heparin binding region of a modified cytokine according to the present invention is the amino acid domain which is responsible for binding GAG, i.e. the GAG binding region. In some embodiments, a modified cytokine according to the present invention has a reduced ability to bind GAG as compared to the corresponding wild type cytokine. In other words, in some embodiments, a modified cytokine according to the present invention has a reduced GAG binding activity as determined by one or more assays known in the art.

In certain examples herein, murine IL-12 and modified forms of murine IL-12 were used as the cytokine sequence because human IL-12 is not active in mice and studies in murine models are necessary. Using murine forms of IL-12 and modified IL-12 allows the testing of the invention in murine models. Such constructions should not be taken to be limiting, and thus, the invention is applicable to other animal systems, e.g. human, etc. and other cytokines, e.g. human GM-CSF, human IL-2, human IL-12, and the like. Additionally, in the examples herein, a human IgG3 sequence was used as the antibody sequence, however, any immunoglobulin isotype or fragments thereof known in the art can be used as the antibody sequence.

Since structural and functional studies have shown that the p35 subunit of IL-12 is responsible for receptor binding and signaling, the carboxy-terminal end of the p40 subunit was analyzed for regions which may be responsible for the ability of IL-12 to bind heparin compounds. After a region was identified as potentially being responsible for the heparin binding activity of IL-12, point mutations in the identified region were constructed and assayed as described herein. FIG. 1 shows the wild type amino acid sequence of a heparin binding region of murine IL-12 p40, i.e. amino acid residues at positions 251 to 260 of Accession Number NP_032378, and the amino acid modifications thereto. The amino acid numbering as used herein is based on the aligned sequences of the mature IL-12 subunit beta proteins encoded by the IL12B genes of various organisms is set forth in FIG. 2.

As used herein, a "heparin binding region of IL-12" includes the amino acid sequences which correspond to amino acid residues 250-261 of Accession Number NP_032378 as aligned in FIG. 2. For example, amino acid residues 253-264 of Accession Number NP_002178 and Accession Number XP_527101, amino acid residues 254-265 of Accession Number NP_001003292 and NP_776781, and amino acid residues 250-261 of Accession Number NP_072133 are heparin binding regions of IL-12.

In some embodiments, IL-12 having one or more of the basic amino acid residues of the wild type heparin binding regions of IL-12 substituted with non-basic amino acid residues are used as the modified cytokine sequence in the Ab-modC proteins. For example, in some embodiments, the modified cytokine sequence of the Ab-modC proteins contain a binding region of IL-12 that corresponds to amino acid residues 250-261 of Accession Number NP_032378, but with a non-basic amino acid substitution at position 254, 255, 256, 260, or a combination thereof.

Thus, in some embodiments, a modified IL-12 sequence of the Ab-modC of the present invention comprises a modified heparin binding region comprising, consisting essentially of, or consisting of the following formula I:

V-X1-X2-Q-X3-K*-X4-X5-X6-X7-K*-X8 (I)

wherein X1 is R or Q,
X2 is V, A, or I,
X3 is G or R*,
X4 is S, N, or K*,
X5 is K*, N, or E,
X6 is R or K,
X7 is E, M, or T, and
X8 is K* or E, and
wherein one or more amino acid residues designated with an "*" are substituted with a non-polar amino acid residue selected from the group consisting of A, G, I, L, M, F, P, and V and other amino acid residues which result in a decrease in heparin binding as compared to the corresponding wild type IL-12. In some embodiments, the modified IL-12 sequence exhibits an immunostimulatory activity which is consistent with the type of the immune response caused by a wild type IL-12 selected from the group consisting of Accession Numbers NP_002178, XP_527101, NP_001003292, NP_776781, NP_032378, NP_072133, NP_998736, NP_001007109, and XP_002666092, which sequences are herein incorporated by reference in their entirety, as determined from in vitro and/or in vivo assays. The immunostimulatory activity of a modified IL-12 sequence may be readily determined using methods known in the art. See e.g. Peng et al. (1999) J Immunol 163:250-8; and Helguera et al. (2006) Vaccine 24:304-16, which are herein incorporated by reference in their entirety. In some embodiments, the Ab-modIL-12 proteins exhibit at least about 10-20%, at least about 20-30%, at least about 30-40%, at least about 40-50%, at least about 50-60%, preferably at least about 60-70%, more preferably at least about 70-80%, even more preferably at least about 80-90%, or most preferably at least about 90-100% of the immunostimulatory activity of a wild type IL-12 selected from the group consisting of Accession Numbers NP_002178, XP_527101, NP_001003292, NP_776781, NP_032378, NP_072133, NP_998736, NP_001007109, and XP_002666092.

In some embodiments, a modified IL-12 sequence of the Ab-modC of the present invention comprises (a) a modified heparin binding region comprising, consisting essentially of, or consisting of the following formula I:

V-X1-X2-Q-X3-K*-X4-X5-X6-X7-K*-X8 (I)

wherein X1 is R or Q,
X2 is V, A, or I,
X3 is G or R*,
X4 is S, N, or K*,
X5 is K*, N, or E,
X6 is R or K,
X7 is E, M, or T, and
X8 is K* or E, and
wherein one or more amino acid residues designated with an "*" are substituted with a non-polar amino acid residue selected from the group consisting of A, G, I, L, M, F, P, and V and other amino acid residues which result in a decrease in heparin binding as compared to the corresponding wild type IL-12, and (b) an amino acid sequence having (1) at least 90%, 91%, 92%, 93%, 94%, 95%, 96%, 97%, 98%, 99%, or 100% identity to KYENYTSSFFIRDIIKPDPPKNLQ (SEQ ID NO:8), or (2) at least 90%, 91%, 92%, 93%, 94%, 95%, 96%, 97%, 98%, 99%, or 100% identity to VEVSWEYPDTWSTPHSYFSL (SEQ ID NO:9). In these embodiments, the modified heparin binding region (a) and the amino acid sequence (b) need not be directly linked to each other and/or in any particular order. For example, one or more intervening amino acid residues may be located between the modified heparin binding region (a) and the amino acid sequence (b) and/or the amino acid sequence (b) may be located before or after the modified heparin binding region (a).

In some embodiments, a modified IL-12 sequence of the Ab-modC of the present invention comprises (a) a modified heparin binding region comprising, consisting essentially of or consisting of the following structural formula I:

V-X1-X2-Q-X3-K*-X4-X5-X6-X7-K*-X8 (I)

wherein X1 is R or Q,
X2 is V, A, or I,
X3 is G or R*,
X4 is S, N, or K*,

X5 is K*, N, or E,
X6 is R or K,
X7 is E, M, or T, and
X8 is K* or E, wherein
wherein one or more amino acid residues designated with an "*" are substituted with a non-polar amino acid residue selected from the group consisting of A, G, I, L, M, F, P, and V and other amino acid residues which result in a decrease in heparin binding as compared to the corresponding wild type IL-12, (b) a first amino acid sequence having at least 90%, 91%, 92%, 93%, 94%, 95%, 96%, 97%, 98%, 99%, or 100% identity to KYENYTSSFFIRDIIKPDPPKNLQ (SEQ ID NO:8), and (c) a second amino acid sequence having at least 90%, 91%, 92%, 93%, 94%, 95%, 96%, 97%, 98%, 99%, or 100% identity to VEVSWEYPDTWSTPHSYFSL (SEQ ID NO:9). In these embodiments, the modified heparin binding region (a), the first amino acid sequence (b), and the second amino acid sequence (c) need not be directly linked to each other and/or in any particular order. For example, (1) one or more intervening amino acid residues may be located between the modified heparin binding region (a) and the first amino acid sequence (b), and/or between the modified heparin binding region (a) and the second amino acid sequence (c), and/or between the first amino acid sequence (b) and the second amino acid sequence (c), and/or (2) the modified heparin binding region (a) may be located before or after the first amino acid sequence (b) and/or the second amino acid sequence (c), e.g. (a)-(b)-(c), (a)-(c)-(b), (b)-(a)-(c), (c)-(a)-(b), (b)-(c)-(a), or (c)-(b)-(a).

In some embodiments, the present invention provides nucleic acid molecules which encode the Ab-modC proteins disclosed herein and their corresponding complementary sequences. In some embodiments, the nucleic acid molecules comprise, consist essentially of, or consist of a sequence (or its complement) which encodes an Ab-modC protein comprising a modified heparin binding region comprising, consisting essentially of or consisting of the above formula I.

In some embodiments, the nucleic acid molecules comprise, consist essentially of, or consist of a sequence (or its complement) which encodes an Ab-modC protein comprising a modified heparin binding region comprising, consisting essentially of or consisting of (a) the above formula I and (b) an amino acid sequence having (1) at least 90%, 91%, 92%, 93%, 94%, 95%, 96%, 97%, 98%, 99%, or 100% identity to KYENYTSSFFIRDIIKPDPPKNLQ (SEQ ID NO:8), and/or (2) at least 90%, 91%, 92%, 93%, 94%, 95%, 96%, 97%, 98%, 99%, or 100% identity to VEVSWEYPDTWSTPHSYFSL (SEQ ID NO:9). As with the polypeptide sequences above, in these embodiments, the nucleotide sequence which codes for the modified heparin binding region (a) and nucleotide sequence which codes for the amino acid sequence (b) need not be directly linked to each other and/or in any particular order.

In some embodiments, the nucleic acid molecules comprise, consist essentially of, or consist of a sequence (or its complement) which encodes an Ab-modC protein comprising a modified heparin binding region comprising, consisting essentially of or consisting of (a) the above formula I and (b) a first amino acid sequence having at least 90%, 91%, 92%, 93%, 94%, 95%, 96%, 97%, 98%, 99%, or 100% identity to KYENYTSSFFIRDIIKPDPPKNLQ (SEQ ID NO:8), and (c) a second amino acid sequence having at least 90%, 91%, 92%, 93%, 94%, 95%, 96%, 97%, 98%, 99%, or 100% identity to VEVSWEYPDTWSTPHSYFSL (SEQ ID NO:9). As with the polypeptide sequences above, in these embodiments, the nucleotide sequence which codes for the modified heparin binding region (a), the first amino acid sequence (b), and the second amino acid sequence (c) need not be directly linked to each other and/or in any particular order.

A first sequence having a given percent (%) sequence identity with respect to a second sequence is defined as the percentage of amino acid residues (or nucleotide bases) in the first sequence that are identical with the amino acid residues (or nucleotide bases) in the second sequence, after aligning the first and second sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN, ALIGN-2, Megalign (DNASTAR) or BLAST (e.g., Blast, Blast-2, WU-Blast-2) software. Those skilled in the art can determine appropriate parameters for measuring alignment, including any algorithms needed to achieve maximal alignment over the full length of the sequences being compared. For example, the % identity values used herein are generated using WU-BLAST-2 (Altschul et al., Methods in Enzymology 266: 460-480 (1996). Most of the WU-BLAST-2 search parameters are set to the default values. For purposes herein, the default parameters of the BLAST alignment tools available online at blast.ncbi.nlm.nih gov/Blast.cgi were used.

In some embodiments, the polypeptides and/or the nucleic acid molecules according to the present invention are isolated and/or purified. An "isolated" nucleic acid molecule or polypeptide refers to a nucleic acid molecule or polypeptide that is in an environment that is different from its native environment in which the nucleic acid molecule or polypeptide naturally occurs. Isolated nucleic acid molecules or polypeptides includes those having nucleotides or amino acids flanking at least one end that is not native to the given nucleic acid molecule or polypeptide. For example, a promoter P for a protein X is inserted at the 5' end of a protein Y which does not natively have P at its 5' end. Protein Y is thus considered to be "isolated". As used herein, a "purified" polypeptide or nucleic acid molecule means that some or all of the components in the composition from which the polypeptide or the nucleic acid molecule was obtained have been removed.

Methods known in the art were used to fuse the antibody sequence to the cytokine sequence to form the Ab-modC proteins of the present invention. See e.g. Dela Cruz et al. (2000) J Immunol 165:5112-21; Penichet et al. (2001) Human Antibodies 10:43-49; Penichet, et al. (2001) J Immunol Methods 248:91-101 (and the references cited therein); and Peng et al. (1999) J Immunol 163:250-8, all of which are incorporated for all purposes herein. An expression vector, known in the art, that encodes the anti-human HER2/neu (Herceptin $V_H$, previously known as humanized 4D5-8 antibody) heavy chain genetically fused to IL-12 p40 subunit was used in the site directed mutagenesis to develop the five anti-HER2/neu-modIL-12 proteins shown in FIG. 1. These new Ab-modC proteins were called: anti-HER2/neu IgG3-(IL-12 mutant R254A), anti-HER2/neu IgG3-(IL-12 mutant K255A), anti-HER2/neu IgG3-(IL-12 mutant K256A), anti-HER2/neu IgG3-(IL-12 mutant K258A), anti-HER2/neu IgG3-(IL-12 mutant K260A). All mutants generated were validated by sequencing and murine myeloma cell lines P3X63Ag8.653 or Sp2/0-Ag14 that produce high levels of the anti-human HER2/neu (Herceptin $V_L$) kappa (κ) light chain were used as recipients for transfection (electroporation) of the vector encoding the anti-human HER2/neu (Herceptin V$_H$) heavy chain with the mutants of IL-12 p40 subunit. Stably transfected cells were isolated using the selectable drug marker histidinol and positive clones were identified by ELISA assay. Secreted proteins were labeled with $^{35}$S-methionine, immunoprecipitated, and analyzed by SDS-PAGE under reducing and non-reducing conditions to verify the expected molecular weight of approximately 310 kDa and confirm their proper assembly and secretion.

Figure 3B:
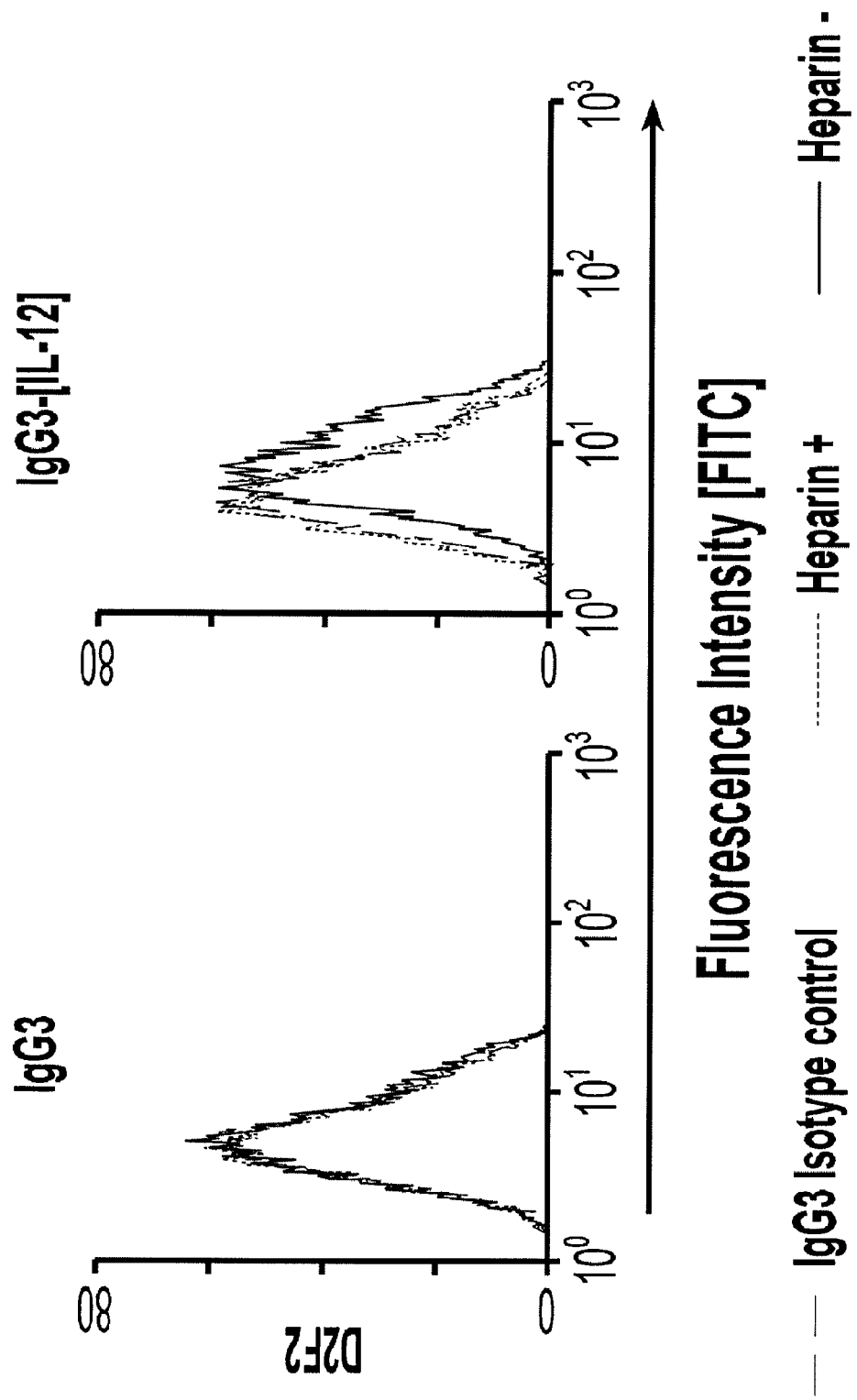
Figure 3B:
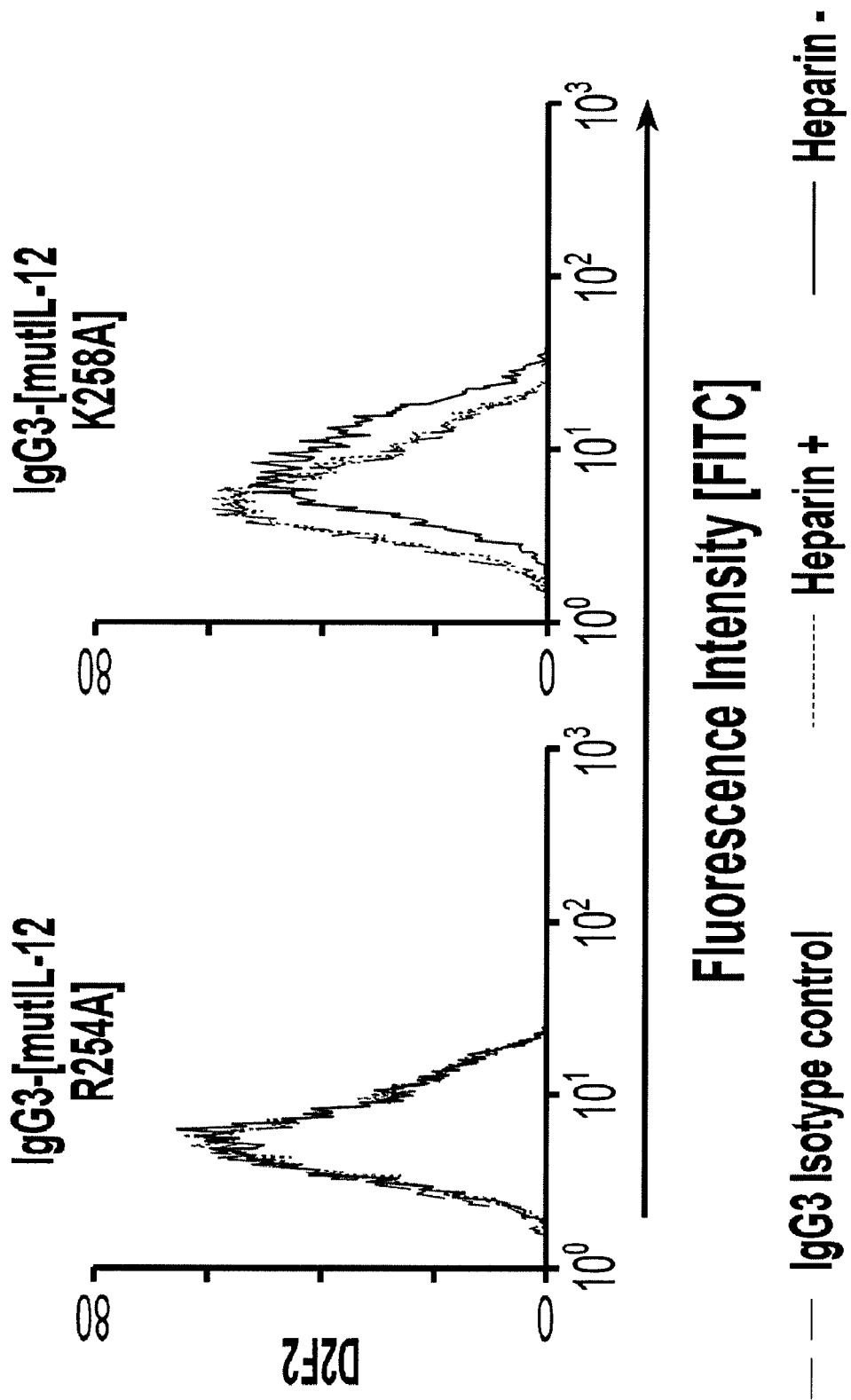
Figure 4A:
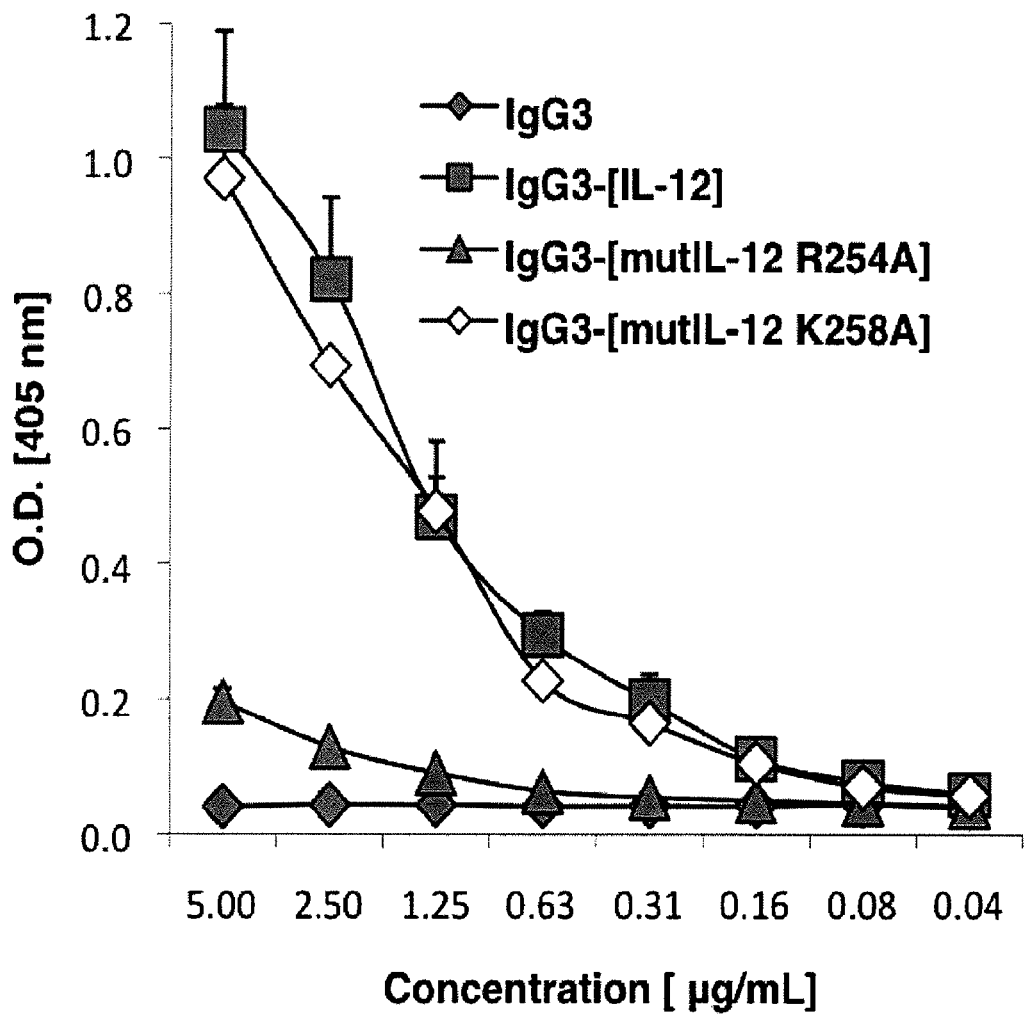
FIG. 4C is a graph showing the heparin binding activity of anti-HER2/neu IgG3-(modIL-12). Low molecular weight heparin was dissolved in PBS at 25 μg/ml and incubated on BD Heparin binding plates overnight at room temperature. The plates coated with heparin were washed with PBS and blocked with 3% BSA in PBS blocking solution for one hour at 37° C., followed by washing with PBS. The proteins were incubated by triplicates using serial 1:2 dilutions ranging from 5-0.04 μg/ml for 2 hours at 37° C. The plates were then washed and incubated with goat anti-human kappa alkaline phosphatase conjugated (dilution 1:30000) for 1 hour at 37° C. After washing with PBS, 1 mg/ml of alkaline phosphatase substrate (p-nitrophenyl phosphate disodium) results in diethanolamine (96% diethanolamine (v/v), 0.24 mM $MgCl_2$, and water (pH 9.8)) was added and incubated 40 minutes at 37° C. before measuring the absorption at 405 nm. The binding was detected using a goat anti-human kappa conjugated to alkaline phosphatase. The absorbance was measured after 60 min incubation with substrate. This study was conducted using purified proteins.
Figure 4B:
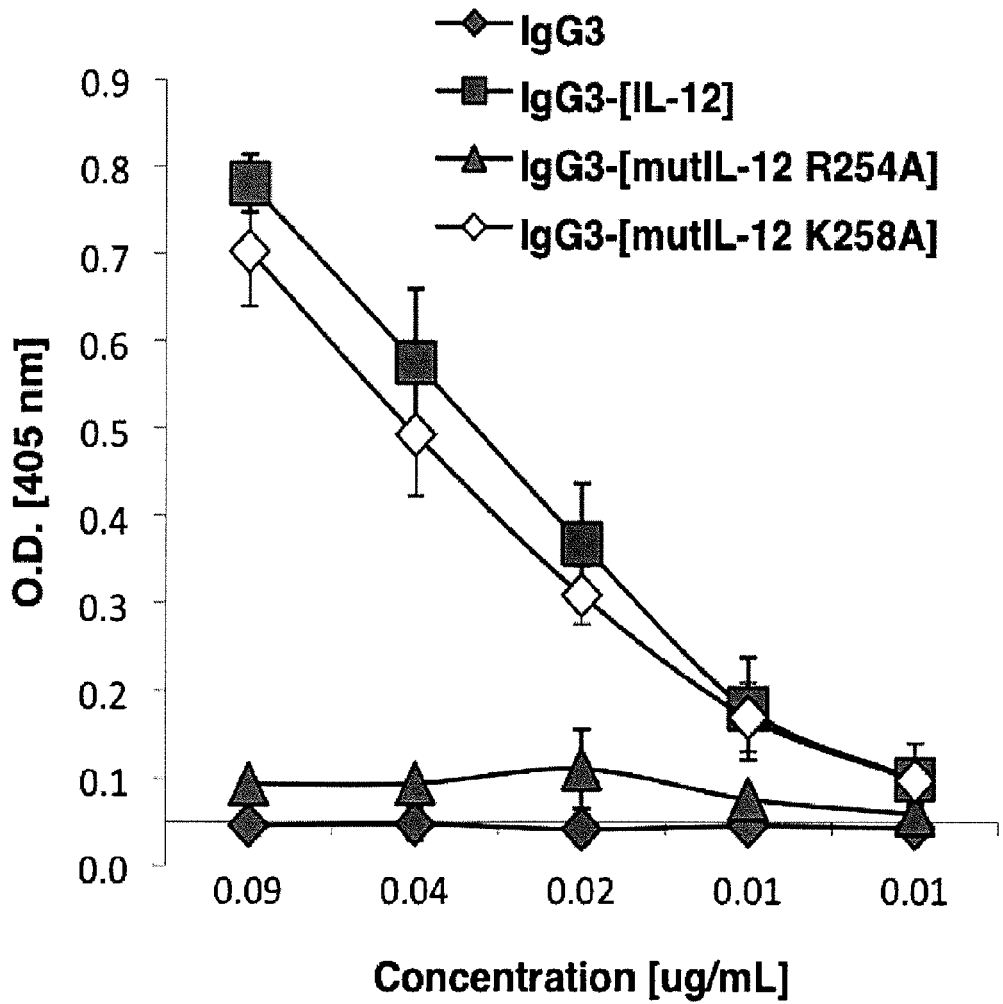

The ability of the Ab-modC proteins to bind GAGs on the surface of the parental tumor cells (D2F2) not expressing HER2/neu was examined by flow cytometry. Consistent with the results observed using supernatant or purified protein, the heparin-binding activity of mutant R254A was significantly decreased and not decreased in the case of mutant K258A compared to the non-mutated IL-12 (wild type). See FIGS. 3A and 3B. The addition of heparin as competitor eliminated the binding of all mutants to a level to D2F2 with anti-HER2/neu IgG3 confirming that the interaction with this HER2/neu negative cell line was due to GAG-binding. The decreased of heparin-binding activity exhibited by mutant R254A was confirmed by ELISA. FIG. 4A shows that the binding of anti-HER2/neu IgG3-(modIL-12) to heparin immobilized on a solid surface was dose-dependent and paralleled the results observed using flow cytometry with purified protein. FIG. 4B shows that the binding of anti-HER2/neu IgG3-(modIL-12) to heparin immobilized on a solid surface was dose-dependent and paralleled the results observed using flow cytometry with supernatant. The heparin-binding properties of mutant R254A was substantially reduced (p<0.033, Student's t-test) compared with the non-mutated IL-12, although the binding was unaffected for mutant K258A. These results are consistent with the possibility that the basic residue arginine 254 plays a major role in the heparin-binding activity of murine IL-12, while lysine 258 seems not to be relevant under the tested conditions.

Figure 3C:
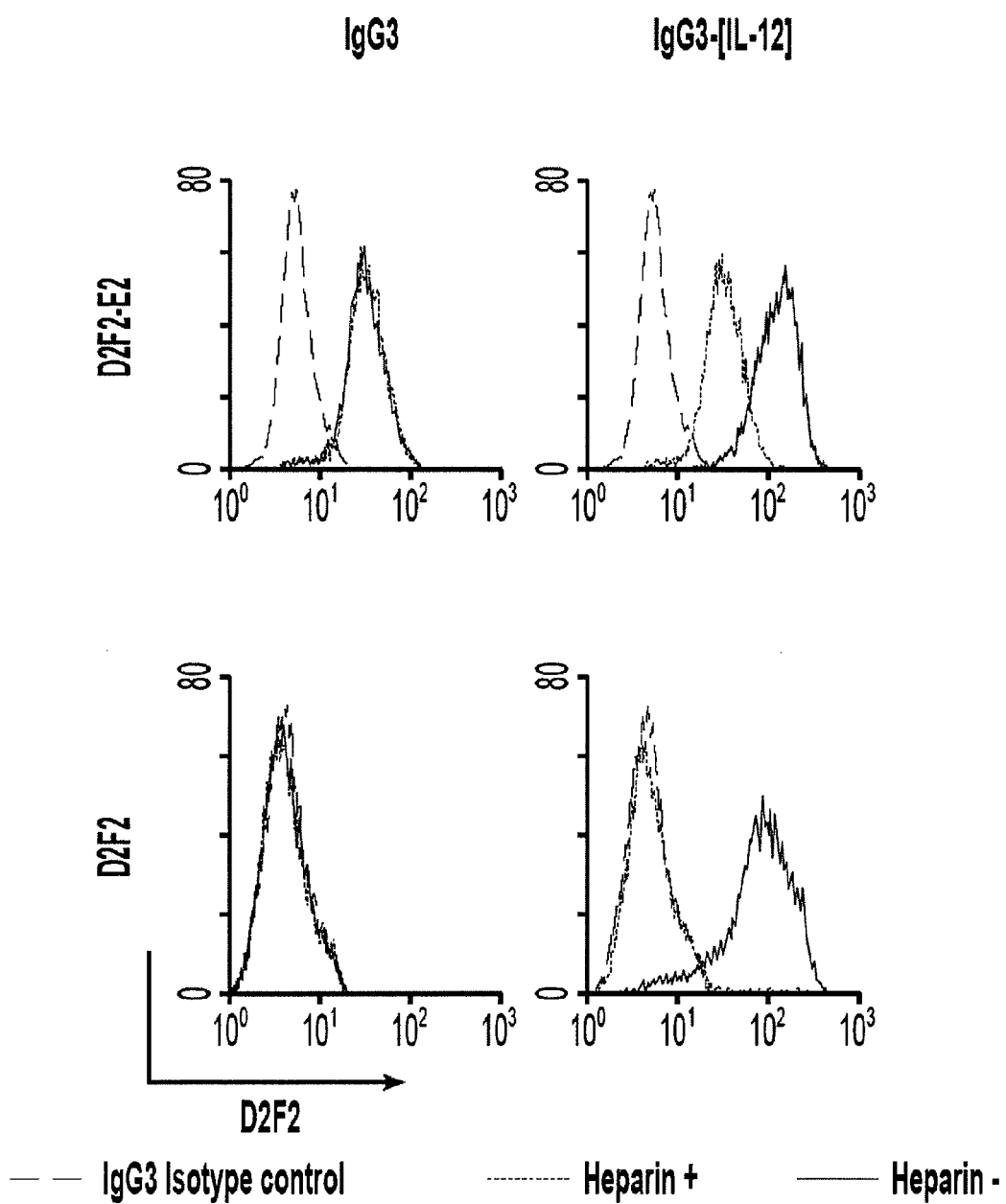
Figure 3C:
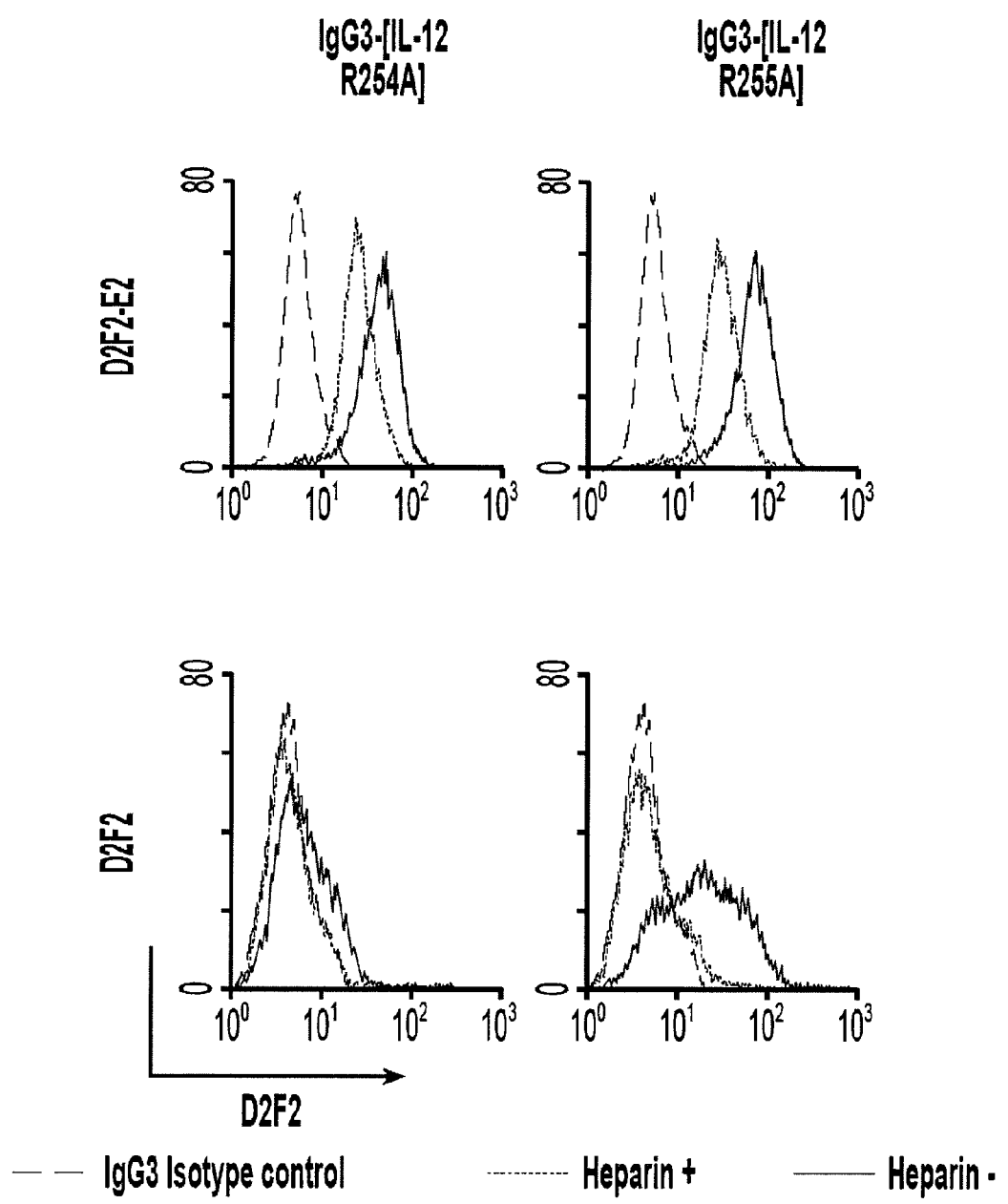
Figure 3C:
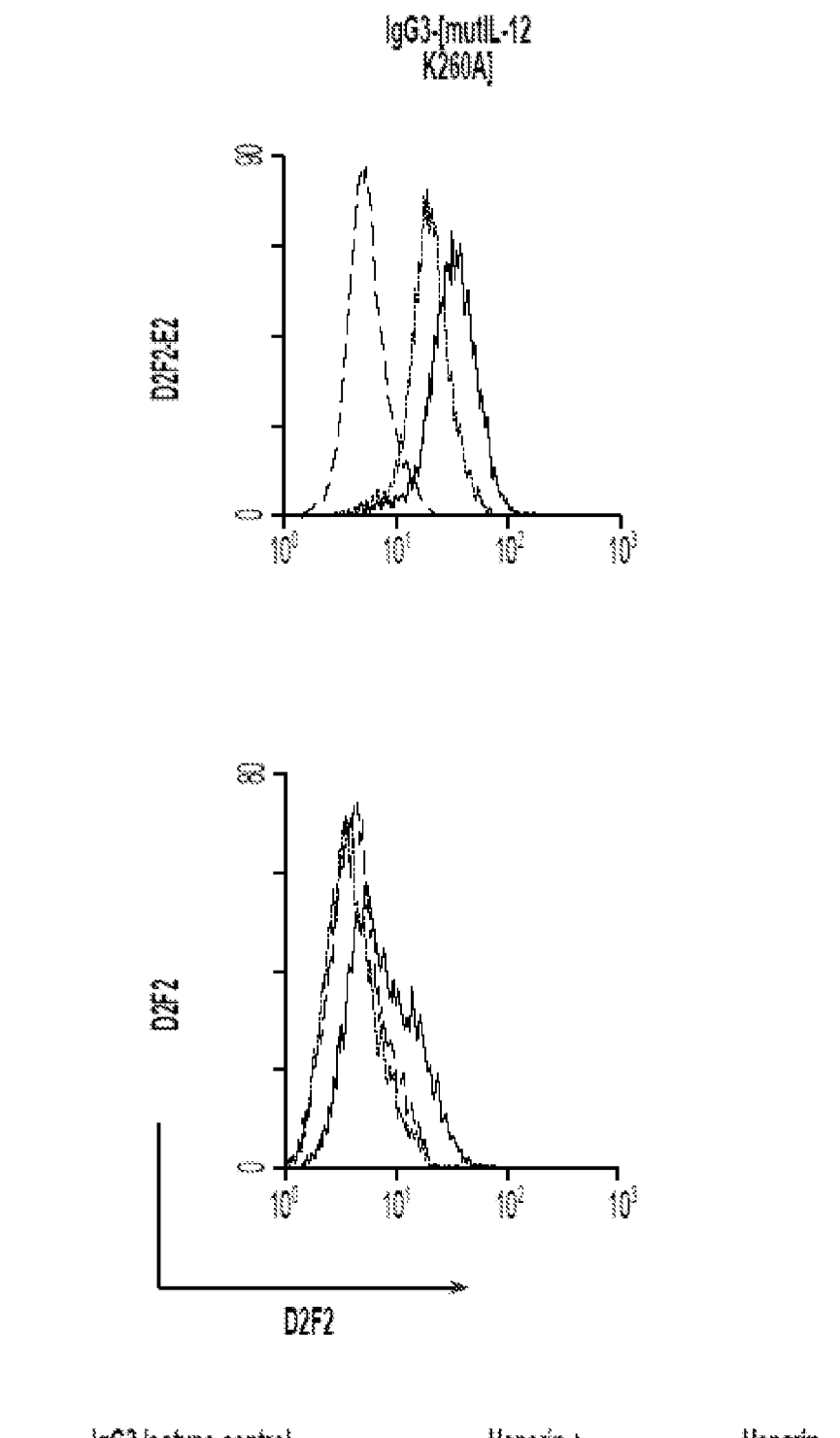
Figure 4C:
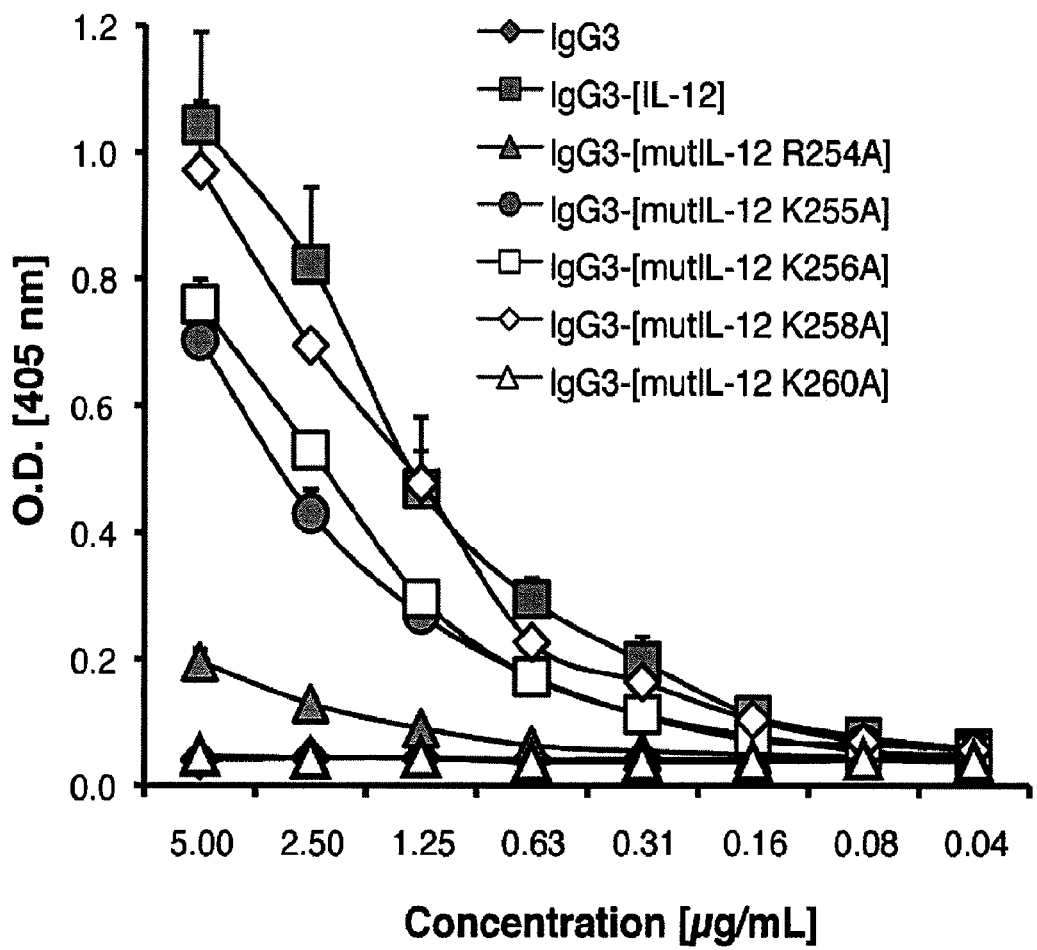

FIG. 3C shows that all anti-HER2/neu IgG3-(modIL-12) retained the capacity to bind to HER2/neu expressed on the surface of the murine mammary cancer cell line D2F2/E2 expressing human HER2/neu. The parental cell line not-expressing HER2/neu (D2F2) was used as negative control of HER2/neu expression. The heparin-binding activity of the non-mutated anti-IgG3-(IL-12) was observed in D2F2 cells was dramatically decreased in the presence of heparin as expected. Importantly, FIG. 4C shows that the heparin-binding activity for both anti-HER2/neu IgG3-(IL-12 mutant R254A) and anti-HER2/neu IgG3-(IL-12 mutant K260A) was reduced. The mutants anti-HER2/neu IgG3-(IL-12 mutant K255A) showed higher binding activity but appear to be reduced, and anti-HER2/neu IgG3-(IL-12 mutant K256A) maintained some binding activity and the mutant anti-HER2/neu IgG3-(IL-12 mutant K258A) did not show any reduction in heparin binding activity.

FIGS. 3C and 4C show an initial comparative study in which all purified anti-HER2/neu IgG3-(modIL-12) proteins were included. However, it has also been observed that the heparin-binding activity exhibited by the anti-HER2/neu IgG3-(modIL-12) proteins varies depending on the assay and batch of protein especially for the case of mutants K255A, K256A and K260A. Therefore, anti-HER2/neu IgG3-(IL-12 mutant R254A) is a preferred Ab-modC protein according to the present invention. Additionally, when these mutants (K255A, K256A and K260A) are tested in tissue culture supernatant no binding to non-HER2/neu expressing cells was detected by flow compared to the wild type IL-12 fusion protein or the mutant K258A.

Therefore, as set forth herein, an Ab-modC protein has a reduced ability to bind heparin compounds when the Ab-modC protein exhibits a reduced ability to bind a heparin compound by at least one heparin binding assay known in the art. In other words, for an Ab-modC protein to be characterized as having a reduced ability to bind a heparin compound, the Ab-modC protein need not exhibit a reduced ability to bind all heparin compounds in all known heparin binding assays. Instead, a given Ab-modC protein characterized as having a reduced ability to bind a heparin compound need only exhibit a reduced ability to bind a given heparin compound in one heparin binding assay, e.g. an ELISA assay or flow cytometry.

In addition, the Ab-modC protein need not exhibit a reduced ability to bind a given heparin compound in all possible formulations in order to be characterized as having a reduced ability to bind heparin compounds. In other words, if the purified form of a given Ab-modC protein exhibits a reduced ability to bind a heparin compound, the given Ab-modC protein need not also exhibit a reduced ability or the same degree of reduction to bind a heparin compound when in a composition comprising other ingredients, e.g. in a supernatant, and vice versa. Thus, according to the present invention, a compound, e.g. protein, having a reduced ability to bind a heparin compound may exhibit results that differ in different preparations, but so long as the compound exhibits a reduced ability to bind a heparin compound in one type of preparation and/or assay, it is considered to have a reduced ability to bind a heparin compound.

Figure 5A:
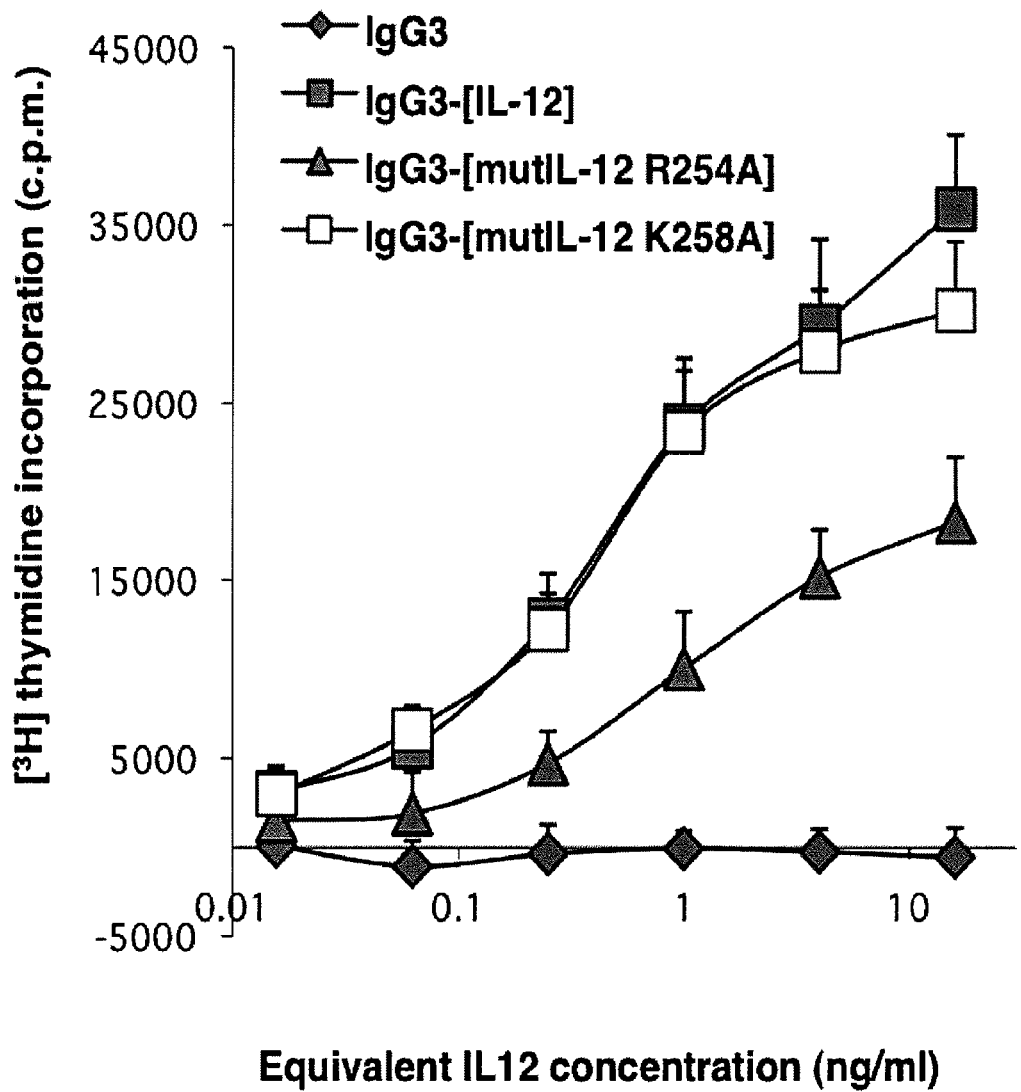
FIG. 5A shows the bioactivity of anti-HER2/neu IgG3-(modIL-12). The bioactivity of modified IL-12 fused to anti-HER2/neu IgG3 was determined by a T-cell proliferation assay known in the art using human peripheral blood mononuclear cells (PBMCs) activated for 3 days in the presence of IL-2 (20 U/ml) and phytohaemagglutinin (PHA) (25 μg/ml). PBMCs were incubated for 2 days with equivalent molar concentrations of anti-HER2/neu IgG3 (IgG3), anti-HER2/neu IgG3-(IL-12), or each one of the anti-HER2/neu IgG3-(modIL-12) (only mutants R254A and K258A are shown) purified proteins. Proliferation was measured by a [$^3$H]-thymidine incorporation assay known in the art. Error bars are mean±SD of quintuplicate measurements. Mutant R254A showed significant values (p≤0.025, Student's t-test) compared to anti-HER2/neu IgG3-(IL-12) positive control. The graph is representative of two independent experiments.
Figure 5B:
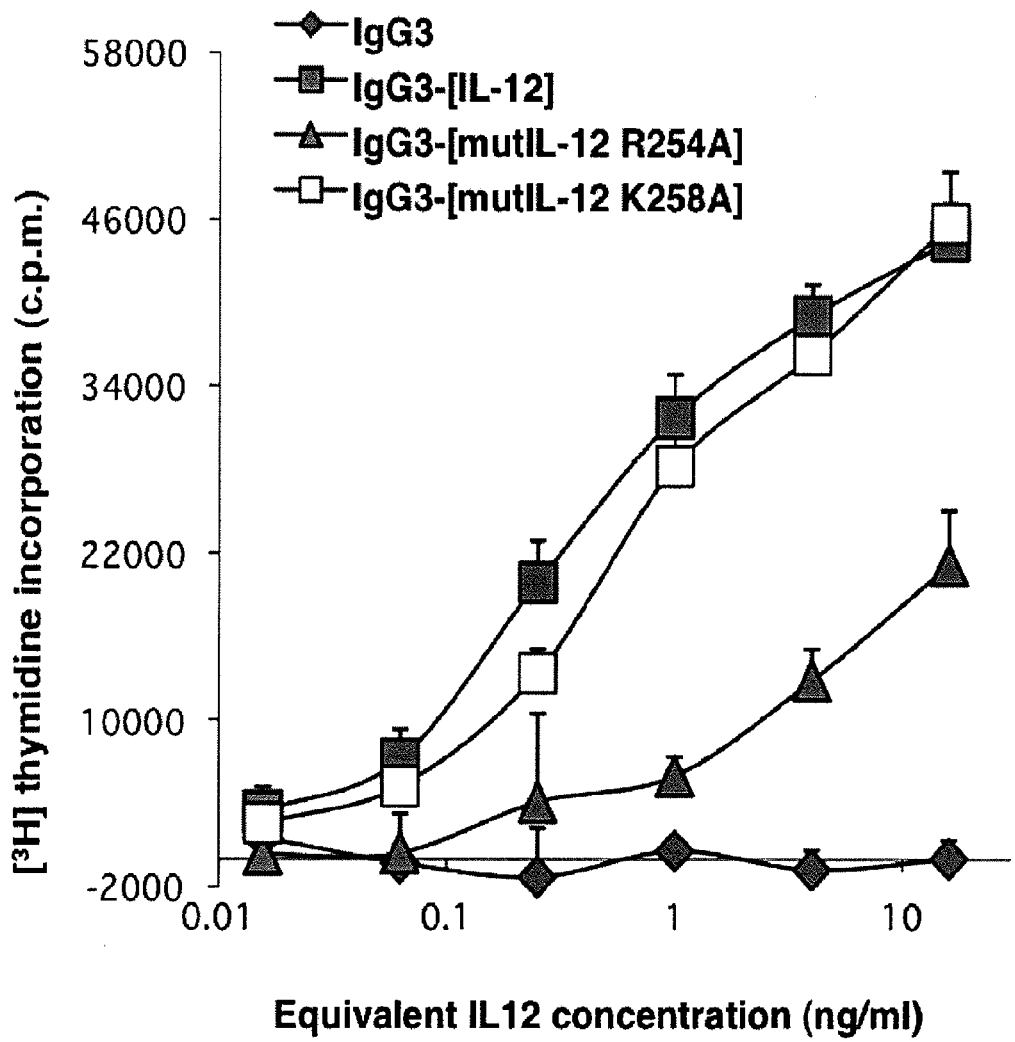
FIG. 5B shows the bioactivity of anti-HER2/neu IgG3-(modIL-12). The bioactivity of modified IL-12 fused to anti-HER2/neu IgG3 was determined by a T-cell proliferation assay known in the art using human PBMCs activated for 3 days in the presence of IL-2 (20 U/ml) and PHA (25 μg/ml). PBMCs were incubated for 2 days with supernatant containing equivalent molar concentrations of anti-HER2/neu IgG3 (IgG3), anti-HER2/neu IgG3-(IL-12), or each one of the anti-HER2/neu IgG3-(modIL-12) (only mutants R254A and K258A are shown) serially diluted 1:4 over a range from 16 ng/ml to 15 pg/ml. Proliferation was measured by a [$^3$H]-thymidine incorporation assay known in the art. This study was conducted using proteins in tissue culture supernatant (before purification). The graph is representative of two independent experiments. Error bars are mean±SD of pentuplicate measurements.
Figure 5C:
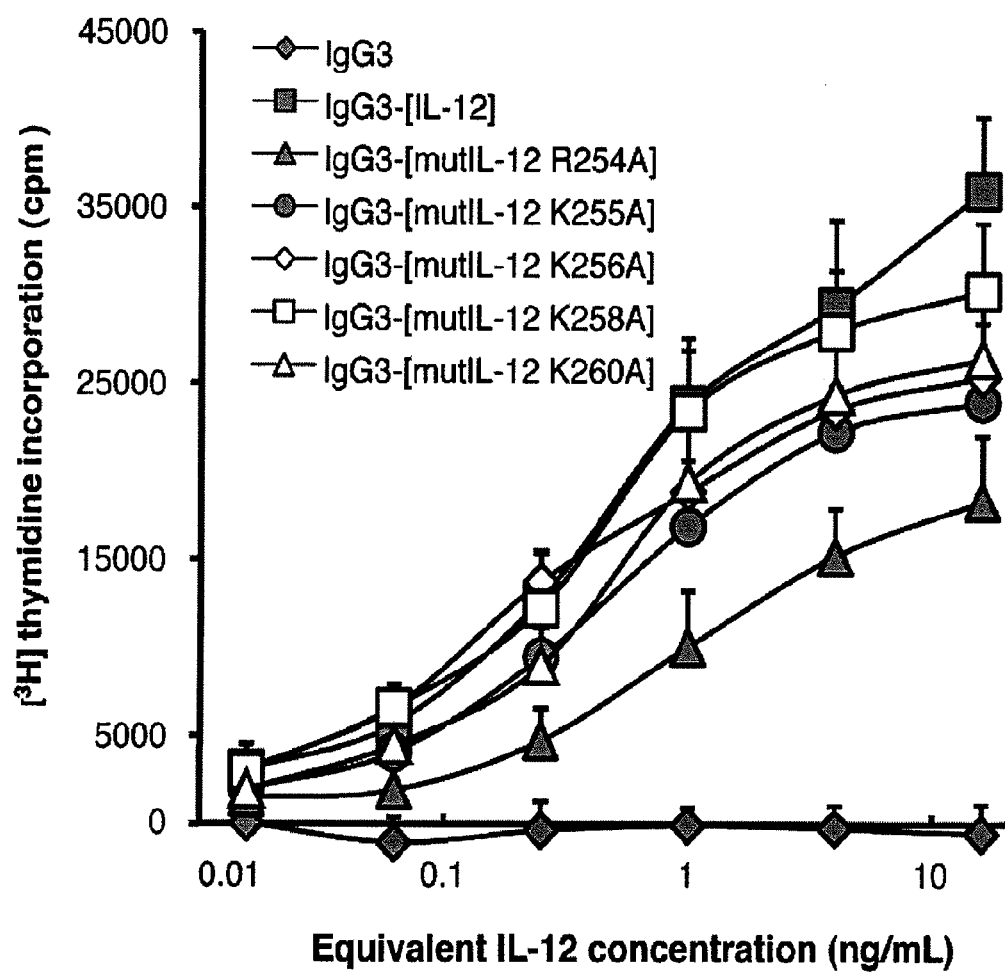
FIG. 5C is a graph showing the bioactivity of anti-HER2/neu IgG3-(modIL-12). The bioactivity of modified IL-12 fused to anti-HER2/neu IgG3 was determined by a T-cell proliferation assayed using human PBMCs activated for 3 days in the presence of IL-2 (20 U/ml) and PHA (25 μg/ml). The PBMCs were washed and incubated and 96-well plates for 2 days at 37° C., 5% $CO_2$ in the presence of equivalent molar concentrations of anti-HER2/neu IgG3 (IgG3), anti-HER2/neu IgG3-(IL-12), or each one of the anti-HER2/neu IgG3-(modIL-12) serially diluted 1:4 over the range from 16 ng/ml to 15 pg/ml. Proliferation was measured by a [$^3$H]-thymidine incorporation assay known in the art. Error bars are mean±SD of pentuplicate measurements. This study was conducted using purified proteins.

A proliferation assay of PHA-activated human lymphoblasts was conducted in order to determine if the mutations affected the bioactivity of murine IL-12. These studies were performed using supernatant or purified protein. All mutants exhibited IL-12 bioactivity in a dose dependent manner. FIG. 5A (purified protein) and FIG. 5B (supernatant) show that the bioactivity of the mutant K258A was preserved when compared with the wild type IL-12. FIG. 5C shows that all anti-HER2/neu IgG3-(modIL-12) retained the IL-12 bioactivity comparing with the IL-12 wild type in the anti-HER2/neu IgG3-(IL-12) protein. Although the mutant R254A showed significant less bioactivity (p<0.025, Student's t-test) compared to the non-mutated IL-12 fusion protein. However, all mutants were capable of significantly inducing the proliferation of T-cells.

Therefore, the present invention provides Ab-modC proteins in which the modified cytokine sequence exhibits a reduced ability to bind a heparin compound, such as heparin, glycosaminoglycan (GAG), heparan sulfate (HS), heparan sulfate proteoglycan (HSPG), perlecan, agrin, collagen XVIII, syndecan, glypican, and the like, as compared to the corresponding wild type cytokine. In some embodiments, the present invention provides Ab-modC proteins in which the modified cytokine sequence exhibits a reduced ability to bind glycosaminoglycans (GAG), such as heparin, as compared to the corresponding wild type cytokine Since the Ab-modC proteins of the present invention exhibit a reduced ability to bind heparin compounds, the Ab-modC proteins may exhibit superior concentration in the microenvironment of the tumor (compared to the fusion proteins with wild type IL-12) when administered systemically and therefore directly enhance the tumoricidal effect of the antibody and/or enhance the activation of a secondary anti-tumor immune response.

In some embodiments, the Ab-modC proteins of the present invention pre-measured and/or prepackaged and/or ready for use without additional measurement or processing. The Ab-modC proteins of the present invention may be provided in kits packaged together with one or more components, e.g. instructions, buffers, reagents, serum proteins, antibodies, substrates, and the like, for the assembly and/or use of the Ab-modC proteins.

In some embodiments, the Ab-modC proteins and the antigen vaccinations are delivered parenterally, e.g. intravenously, intraperitoneally, intramuscularly, or subcutaneously, to a subject. Generally, the delivered dose is sufficient to elicit the desired effect in the subject, e.g. elicitation of humoral and/or cellular immune responses against the target antigen, anti-tumor activity, anti-infection activity, and the like. The dosages may be optimized for an individual subject based upon, e.g. the subject's age, gender, species, and weight, as well the extent or presence of the disease state to be treated (either therapeutically or prophylactically) using methods known in the art. In some embodiments, the dosage of the Ab-modC proteins ranges from less than 0.1 mg/kg subject weight to 200 mg/kg subject weight or more. The dosage regime may be tailored or modified according to the subject's response and the desired result, e.g. a single dose or multiple doses may be given over a course of treatment and the dosage and/or timing of dosages may be increased or altered over the course of treatment.

In some embodiments, the Ab-modC proteins are delivered to subjects via ex vivo methods known in the art. For example, one or more cells or a population of cells of interest of the subject, e.g. dendritic cells, antigen presenting cells, and the like, are obtained or removed from the subject and contacted with an amount of an Ab-modC protein of the invention. The contacted cells are then administered to the subject. In some embodiments, the Ab-modC proteins of the present invention may be delivered to a particular site in the subject, e.g. a site of need such as a tumor or infection site, or a given body part or tissue. If desired, the contacted cells may be deposited, injected, grafted, etc. onto a tissue, organ, or a particular site of interest in the subject using methods known in the art. The Ab-modC proteins of the present invention may be used to elicit an immune response against target antigens of various tumors and/or infectious agents. See e.g. U.S. Pat. No. 7,736,652, which is herein incorporated by reference.

Although the Ab-modC proteins of the present invention may be used in conjunction with a target antigen to elicit a humoral and/or cellular immune response against a tumor or infectious agent expressing the target antigen, the Ab-modC proteins of the present invention may be administered without a target antigen for direct targeting of a tumor or an infectious agent expressing the target antigen.

As provided herein, the Ab-modC proteins exhibit an increased ability to target their target antigens due to their reduced ability to bind heparin compounds. Specifically, the reduced ability of the modified cytokines to bind heparin compounds prevents and/or reduces nonspecific binding of the Ab-modC proteins to cells and their extracellular matrices which contain heparin compounds, but do not express the target antigen or cytokine receptor, thereby allowing the Ab-modC proteins to specifically target cells expressing the target antigen and APCs expressing the cytokine receptor with higher efficiencies than the corresponding wild type cytokine fusion proteins. As such, the Ab-modC proteins according to the present invention may be administered to subjects in amounts that are less than that of the corresponding wild type cytokine fusion proteins, yet achieve the same or substantially similar therapeutic response and/or result in a reduction in side effects as compared to the corresponding wild type cytokine fusion proteins. Since the Ab-modC proteins of the present invention are expected to be retained less throughout the body of a subject when administered one or more Ab-modC proteins of the present invention, a reduced systemic toxicity is also expected. Therefore, the present invention also provides methods of stimulating an immune response in a subject while reducing systemic toxicity in the subject by administering one or more Ab-modC proteins of the present invention.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A polypeptide which comprises an antibody sequence, said antibody sequence specific for a tumor associated antigen, linked or fused to a modified cytokine which (a) has a modified heparin binding region which disrupts, inhibits, or reduces the ability of the cytokine to bind a heparin compound as compared to an unmodified heparin binding region of the wild type cytokine corresponding to the modified cytokine, and (b) exhibits immunostimulatory activity which is the same, more than, or less than that of the wild-type cytokine, wherein the wild type cytokine is IL-12.

2. The polypeptide of claim 1, wherein the unmodified heparin binding region consists of

| | |
|---|---|
| VQVQGKSKREKK, | (SEQ ID NO: 10) |
| VQAQGKNNREKK, | (SEQ ID NO: 11) |
| VQVQGKNKREKK, | (SEQ ID NO: 12) |
| VRIQRKKEKMKE or | (SEQ ID NO: 13) |
| VRIQRKKEKTKE. | (SEQ ID NO: 14) |

3. The polypeptide of claim 1, wherein the antibody sequence is that of a human antibody or a human chimeric antibody.

4. The polypeptide of claim 1, wherein the wild type cytokine is a human cytokine.

5. The polypeptide of claim 1, wherein the modified heparin binding region does not significantly or substantially reduce the immunostimulatory activity of the modified cytokine.

6. The polypeptide of claim 1, wherein the modified heparin binding region of the polypeptide consists essentially of or consists of the following formula I:

V-X1-X2-Q-X3-K*-X4-X5-X6-X7-K*-X8  (I)

wherein X1 is R or Q,
X2 is V, A, or I,
X3 is G or R*,
X4 is S, N, or K*,
X5 is K*, N, or E,
X6 is R or K,
X7 is E, M, or T, and
X8 is K* or E, and
wherein one or more amino acid residues designated with an "*" are substituted with a non-polar amino acid residue selected from the group consisting of A, G, I, L, M, F, P, and V, and wherein the modified cytokine having the modified heparin binding region exhibits a decrease in heparin binding as compared to the corresponding wild type cytokine which is IL-12.

7. The polypeptide of claim 6, wherein the modified cytokine further comprises a first amino acid sequence having at least 90%, 91%, 92%, 93%, 94%, 95%, 96%, 97%, 98%, 99%, or 100% identity to KYENYTSSFFIRDIIKPDPP-KNLQ (SEQ ID NO:8), and/or a second amino acid sequence having at least 90%, 91%, 92%, 93%, 94%, 95%, 96%, 97%, 98%, 99%, or 100% identity to VEVSWEYPDTWSTPH-SYFSL (SEQ ID NO:9).

8. A composition or kit which comprises the polypeptide according to claim 6.

9. The polypeptide of claim 3, wherein the antibody is specific for epidermal growth factor receptor (EGFR), transferrin receptor (CD71), mucin 1 (MUC1), prostate-specific membrane antigen (PMSA), CD19, CD20, CD33, CD40, CD52, or HER2/neu.

10. A polypeptide which comprises an antibody linked or fused to a modified cytokine which has a modified heparin binding region, wherein
said antibody is specific for an antigen associated with a tumor;
said modified heparin binding region comprises the following formula I:

V-X1-X2-Q-X3-K*-X4-X5-X6-X7-K*-X8  (I)

wherein X1 is R or Q,
X2 is V, A, or I,
X3 is G or R*,
X4 is S, N, or K*,
X5 is K*, N, or E,
X6 is R or K,
X7 is E, M, or T, and
X8 is K* or E, and
wherein one or more amino acid residues designated with an "*" are substituted with a non-polar amino acid residue selected from the group consisting of A, G, I, L, M, F, P, and V; and
said modified cytokine having the modified heparin binding region exhibits a decrease in heparin binding as compared to the corresponding wild type cytokine which is IL-12.

11. The polypeptide of claim 10, wherein the antibody is specific for epidermal growth factor receptor (EGFR), transferrin receptor (CD71), mucin 1 (MUC1), prostate-specific membrane antigen (PMSA), CD19, CD20, CD33, CD40, CD52, or HER2/neu.

12. The polypeptide of claim 10, wherein the modified cytokine further comprises a first amino acid sequence having at least 90%, 91%, 92%, 93%, 94%, 95%, 96%, 97%, 98%, 99%, or 100% identity to KYENYTSSFFIRDIIKPDPP-KNLQ (SEQ ID NO:8), and/or a second amino acid sequence having at least 90%, 91%, 92%, 93%, 94%, 95%, 96%, 97%, 98%, 99%, or 100% identity to VEVSWEYPDTWSTPH-SYFSL (SEQ ID NO:9).

13. The polypeptide of claim 10, wherein the one or more amino acid residues designated with an "*" are alanine.

14. The polypeptide of claim 10, wherein amino acid residue X3 is alanine.

15. A composition or kit which comprises the polypeptide according to claim 10.

16. The polypeptide of claim 6, wherein the one or more amino acid residues designated with an "*" are alanine.

17. The polypeptide of claim 6, wherein amino acid residue X3 is alanine.

* * * * *